United States Patent
McInnes et al.

(10) Patent No.: US 12,415,822 B2
(45) Date of Patent: *Sep. 16, 2025

(54) SMALL MOLECULE INHIBITORS SELECTIVE FOR POLO-LIKE KINASE PROTEIN

(71) Applicant: UNIVERSITY OF SOUTH CAROLINA, Columbia, SC (US)

(72) Inventors: Campbell McInnes, Irmo, SC (US); Sandra Navonne Craig, Ellerbe, NC (US)

(73) Assignee: University of South Carolina, Columbia, SC (US)

( * ) Notice: Subject to any disclaimer, the term of this patent is extended or adjusted under 35 U.S.C. 154(b) by 373 days.

This patent is subject to a terminal disclaimer.

(21) Appl. No.: 18/106,543

(22) Filed: Feb. 7, 2023

(65) Prior Publication Data

US 2024/0025930 A1 Jan. 25, 2024

Related U.S. Application Data

(63) Continuation of application No. 17/001,167, filed on Aug. 24, 2020, now Pat. No. 11,597,737, which is a continuation of application No. 15/479,373, filed on Apr. 5, 2017, now abandoned.

(60) Provisional application No. 62/318,439, filed on Apr. 5, 2016.

(51) Int. Cl.
| | | |
|---|---|---|
| A61K 31/167 | (2006.01) | |
| A61K 31/196 | (2006.01) | |
| A61P 35/00 | (2006.01) | |
| A61P 35/04 | (2006.01) | |
| C07C 233/66 | (2006.01) | |
| C07C 233/80 | (2006.01) | |
| C07C 233/81 | (2006.01) | |
| C07C 235/84 | (2006.01) | |
| C07C 311/46 | (2006.01) | |
| C07F 5/04 | (2006.01) | |
| C07F 9/22 | (2006.01) | |

(52) U.S. Cl.
CPC ............. *C07F 9/222* (2013.01); *A61P 35/00* (2018.01); *C07C 233/66* (2013.01); *C07C 233/80* (2013.01); *C07C 233/81* (2013.01); *C07C 235/84* (2013.01); *C07C 311/46* (2013.01); *C07F 5/04* (2013.01); *A61K 31/167* (2013.01); *A61K 31/196* (2013.01); *A61P 35/04* (2018.01)

(58) Field of Classification Search
CPC ........ A61P 35/00; A61P 35/04; A61K 31/167; A61K 31/196; C07F 9/222; C07F 5/04; C07F 9/12; C07C 233/66; C07C 233/80; C07C 233/81; C07C 235/84; C07C 311/46; C07C 229/56; C07C 235/56

See application file for complete search history.

(56) References Cited

U.S. PATENT DOCUMENTS

| | | |
|---|---|---|
| 7,432,260 B2 | 10/2008 | Wang et al. |
| 7,449,544 B2 | 11/2008 | Zheleva et al. |
| 7,576,091 B2 | 8/2009 | McInnes et al. |
| 7,897,605 B2 | 3/2011 | Wang et al. |
| 8,566,072 B2 | 10/2013 | McInnes et al. |
| 9,175,375 B2 | 11/2015 | Kim et al. |
| 9,328,139 B2 | 5/2016 | McInnes et al. |
| 9,376,465 B2 | 6/2016 | McInnes et al. |
| 9,982,015 B2 | 5/2018 | McInnes et al. |
| 10,067,131 B2 | 9/2018 | McInnes et al. |
| 2003/0036628 A1 | 2/2003 | Zheleva et al. |
| 2006/0040997 A1 | 2/2006 | McInnes et al. |
| 2006/0281687 A1 | 12/2006 | Andrews et al. |
| 2006/0293245 A1 | 12/2006 | Zheleva et al. |
| 2008/0132484 A1 | 6/2008 | McInnes et al. |
| 2008/0167385 A1 | 7/2008 | Kontopidis et al. |
| 2009/0215805 A1 | 8/2009 | Wood et al. |
| 2013/0289240 A1 | 10/2013 | McInnes et al. |
| 2014/0228405 A1* | 8/2014 | Tomita ............... C07D 295/135 564/123 |

(Continued)

FOREIGN PATENT DOCUMENTS

| | | |
|---|---|---|
| JP | 60097946 | 5/1985 |
| JP | 2002193800 A | 7/2002 |

(Continued)

OTHER PUBLICATIONS

Imaki et al. al. "Non-peptidic Inhibitors of Human Neutrophil Elastase: The Design and Synthesis of Sulfonanilide-Containing Inhibitors." Bioorg. Med. Chem. 1996, 4, 2115-2134. (Year: 1996).*

(Continued)

*Primary Examiner* — Amanda L. Aguirre

(74) *Attorney, Agent, or Firm* — DORITY & MANNING, P.A.

(57) ABSTRACT

Disclosed are small molecule PLK inhibitors that can target the polo box domain (PBD). Inhibitors can have an atomic mass of about 1000 Da or less and a general structure of

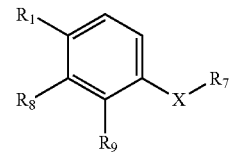

For instance, the inhibitors can include an alkyl benzamido benzoic acid core structure.

13 Claims, 11 Drawing Sheets

Specification includes a Sequence Listing.

(56) References Cited

U.S. PATENT DOCUMENTS

| | | | |
|---|---|---|---|
| 2014/0296484 A1 | 10/2014 | McInnes et al. | |
| 2016/0011195 A1 | 1/2016 | McInnes et al. | |
| 2016/0304485 A1 | 10/2016 | Nikolovska-Coleska et al. | |
| 2017/0283445 A1 | 10/2017 | McInnes et al. | |

FOREIGN PATENT DOCUMENTS

| | | | | |
|---|---|---|---|---|
| WO | WO-9803516 A1 | * | 1/1998 | ............... C07F 9/301 |
| WO | WO-0206189 A2 | * | 1/2002 | ............ C07C 233/29 |
| WO | WO-2007009083 A2 | * | 1/2007 | ............ C07C 243/38 |
| WO | WO-2011083304 A1 | * | 7/2011 | ............ A61K 31/485 |
| WO | WO-2011091213 A2 | * | 7/2011 | ............ A61K 31/164 |
| WO | WO-2015040425 A1 | * | 3/2015 | ............ C07C 235/64 |
| WO | WO-2016166604 A1 | * | 10/2016 | ............... A61P 35/00 |
| WO | WO-2018035072 A1 | * | 2/2018 | ............... A61P 35/00 |

OTHER PUBLICATIONS

Lee et al. "Targeting Aurora Kinases for the Treatment of Prostate Cancer." Cancer Res. 2006, 66, 4996. (Year: 2006).*

Perera et al. "Oncogenic KRAS triggers MAPK-dependent errors in mitosis and MYC-dependent sensitivity to anti-mitotic agents." Sci. Rep. 2016, 6, 29741. (Year: 2016).*

Burkard et al. "Enabling and disabling Polo-like kinase 1 inhibition through chemical genetics" *ACS Chem. Biol.* 7 (2012) pp. 978-981.

Chapagai. J. Med. Chem . 2021, 64, 9916-9925 (Year: 2021).

Dai et al. "Polo-like kinases and centrosome regulation" *Oncogene* 21 (2002) pp. 6195-6200.

De Carcer et al. "From Plk1 to Plk5: Functional evolution of polo-like kinases" *Cell Cycle* 10 (2011) pp. 2255-2262.

Eckerdt et al. "Polo-like kinases and oncogenesis" *Oncogene* 24 (2005) pp. 267-276.

Fisher et al. "The functions of Polo-like kinases and their relevance to human disease" *Curr. Medicinal Chem.—Immun. Endo. Metab. Agents* 2 (2002) pp. 125-134. (Abstract only).

Garland et al. "A phase I pharmacokinetic study of HMN-214, a novel oral stilbene derivative with polo-like kinase-1-interacting properties, in patients with advanced solid tumors" *Clin. Canc. Res.* 12 (2006) pp. 5182-5189.

Holtrich et al. "Induction and down-regulation of PLK, a human serine/threonine kinase expressed in proliferating cells and tumors" *PNAS* 91 (1994) pp. 1736-1740.

Iwaki et al.. Bioorg . Med . Chem . Lett 2019, 29, 1601-1604 (Year: 2019).

Jiang et al. "PI3K/PTEN signaling in angiogenesis and tumorigenesis" *Adv. Canc. Res.* 102 (2009) pp. 19-65.

Kim et al. "Structural analysis of the polo-box domain of human Polo-like kinase 2" *Proteins* 83 (2015) pp. 1201-1208.

Kotani et al. "PKA and MPF-activated Polo-like kinase regulate anaphase-promoting complex activity and mitosis progression" *Molec. Cell* 1 (1998) pp. 371-380.

Lansing et al. "In vitro biological activity of a novel small-molecule inhibitor of polo-like kinase 1" *Molec. Canc. Therapeut.* 6 (2007) pp. 450-459.

Liu et al. "Polo-like kinase 1 facilitates loss of Pten tumor suppressor-induced prostate cancer formation" *J. Biol. Chem.* 286 (2011) pp. 35795-35800.

Lu et al. "The Plk1 inhibitor BI 2536 temporarily arrests primary cardiac fibroblasts in mitosis and generates aneuploidy in vitro" *PLOS One* 5:e12963 (2010) pp. 1-10.

Luo et al. "A genome-wide RNAi screen identifies multiple synthetic lethal interactions with the Ras oncogene" *Cell* 137 (2009) pp. 835-848.

Ma et al. "Role of Plk2 (Snk) in mouse development and cell proliferation" *Molec. Cell. Biol.* 19 (2003) pp. 6936-6943.

McInnes et al. "Targeting subcellular localization through the polo-box domain: Non-ATP competitive inhibitors recapitulate a PLK1 phenotype" *Molec. Canc. Therapeut.* 11 (2012) pp. 1683-1692.

Mross et al. "Phase I dose escalation and pharmacokinetic study of BI 2536, a novel Polo-like kinase 1 inhibitor, in patients with advanced solid tumors" *J. Clin. Oncol.* 26 (2008) pp. 5511-5517.

Mundt et al. "On the regulation and function of human polo-like kinase 1 (PLK1): Effects of overexpression on cell cycle progression" *Biochem. Biophys. Res. Comm.* 239 (1997) pp. 377-385.

Olmos et al. "Phase I study of GSK461364, a specific and competitive Polo-like kinase 1 inhibitor, in patients with advanced solid malignancies" *Clin. Canc. Res.* 17 (2011) pp. 3420-3430.

Qian et al. "Activated Polo-like kinase Plx1 is required at multiple points during mitosis in Xenopus laevie" *Molec. Cell. Biol.* 18 (1998) pp. 4262-4271.

Rudolph et al. "Characterization of BI 6727, a novel Polo-like kinase inhibitor with a distinct pharmacokinetic profile and efficacy in a model of taxane-resistant colon cancer" *20th EORTC* (2008). (Abstract only).

Rudolph et al. "BI 6727, a Polo-like kinase inhibitor with improved pharmacokinetic profile and broad antitumor activity" *Clin. Canc. Res.* 15 (2009) pp. 3094-3102.

Santamaria et al. "Use of the novel Plk1 inhibitor ZK-thiazolidinone to elucidate functions of Plk1 in early and late stages of mitosis" *Molec. Biol. Cell* 18 (2007) pp. 4024-4036.

Schoffski et al. "Multicentric parallel phase II trial of the polo-like kinase 1 inhibitor BI 2536 in patients with advanced head and neck cancer, breast cancer, ovarian cancer, soft tissue sarcoma and melanoma" *Eur. J. Canc.* 46 (2010) pp. 2206-2215.

Sebastian et al. "The efficacy and safety of BI 2536, a novel Plk-1 inhibitor, in patients with stage IIIB/IV non-small cell lung cancer who had relapsed after, or failed, chemotherapy: results from an open-label, randomized phase II clinical trial" *J. Thor. Oncol.* 5 (2010) pp. 1060-1067.

Simmons et al. "Identification of early-growth-response gene encoding a novel putative protein kinase" *Molec. Cell. Biol.* 12 (1992) pp. 4164-4169.

Stadler et al. "An open-label, single-arm, phase 2 trial of the polo-like kinase inhibitor volasertib (BI 6727) in patients with locally advanced or metastatic urothelial cancer" *Cancer* 120 (2014) pp. 976-982.

Steegmaier et al. "BI 2536, a potent and selective inhibitor of polo-like kinase 1, inhibits tumor growth in vivo" *Curr. Biol.* 17 (2007) pp. 316-322.

STN. "Chemical Abstract Database: C22 H29 N O" Reg. No. 887633-16-1 (2006) pp. 1-2.

STN. "Chemical Abstract Database: C21 H27 N O" Reg. No. 887632-97-5 (2006) pp. 3-5.

STN. "Chemical Abstract Database: C20 H24 Br N O2" Reg. No. 447442-39-9 (2002) pp. 1-3.

STN. "Chemical Abstract Database: C19 H18 F N O" Reg. No. 439097-39-9 (2002) pp. 1-2.

STN. "Chemical Abstract Database: C20 H21 N O" Reg. No. 439097-36-6 (2002) pp. 3-5.

STN. "Chemical Abstract Database: C17 H17 N O4" Reg. No. 312533-64-5 (2001) pp. 1-3.

STN. "Chemical Abstract Database: C19 H21 N O3" Reg. No. 117145-68-3 (1988) p. 1.

STN. "Chemical Abstract Database: C16 H15 N O3" Reg. No. 37619-17-3 (1984) p. 1.

STN. "Chemical Abstract Database: C16 H14 Cl N O3" Reg. No. 19921-10-9 (1984) p. 1.

Strebhardt et al. "Targeting polo-like kinase 1 for cancer therapy" *Nat. Rev.* 6 (2006) pp. 321-330.

To et al. "Volasertib (BI 6727), a novel polo-like kinase inhibitor, reverses ABCB1 and ABCG2-mediated multidrug resistance in cancer cells" *J. Canc. Therapeut. Res.* 2 (2013) pp. 1-11.

Wada et al., Jp 2002-193800 A. Partial English Mach Ine Translation (Online)(Retr Ieved On Oct. 20, 2022) <Https:// Worldw Ide .Espacenet.Com/> (Year: 2022).

Weichert et al. "Expression patterns of polo-like kinase 1 in human gastric cancer" *Canc. Sci.* 97 (2006) pp. 271-276.

Winkles et al. "Differential regulation of polo-like kinase 1, 2, 3, and 4 gene expression in mammalian cells and tissues" *Oncogene* 24 (2005) pp. 260-266.

Yang et al.. Dev . Biol. 2015, 404, 49-60 (Year: 2015).

(56) References Cited

OTHER PUBLICATIONS

Zimmerman et al. "Polo-like kinase 3 is required for entry into S phase" *PNAS* 104 (2007) pp. 1847-1852.

* cited by examiner

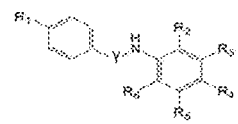

Structure activity of 2-(4-alkylbenzamido)benzoic acid PBD Inhibitors

| SCCP ID | R1 | R2 | R3 | R4 | R5 | R6 | Y | PLK1 PBD IC$_{50}$ (mM) | PLK3 PBD IC$_{50}$ (mM) |
|---|---|---|---|---|---|---|---|---|---|
| 5880 | butyl | H | H | COO⁻ | H | H | C=O | >600 | ND |
| 5881 | hexyl | COO⁻ | H | H | H | H | C=O | 18.4 ± 5.3 | 18.04 ± 5.18 |
| 5903 | hexyl | H | COO⁻ | H | H | H | C=O | 129.8 ± 3.6 | 43.62 ± 1.69 |
| 5905 | pentyl | COO⁻ | H | H | H | H | C=O | 223.6 ± 4.88 | ND |
| 5908 | hexyl | H | SO$_2$NH$_2$ | H | H | H | C=O | >600 | ND |
| 5910 | hexyl | COO⁻ | H | H | OCH$_3$ | OCH$_3$ | C=O | 107.4 | ND |
| 5911 | octyl | COO⁻ | H | H | OCH$_3$ | OCH$_3$ | C=O | 119.5 | ND |
| 5912 | octyl | COO⁻ | H | H | H | H | C=O | 11.27 ± 2.7 | 15.48 ± 0.01 |
| 5914 | octyl | COOC$_2$H$_5$ | H | H | H | H | C=O | >600 | ND |
| 5915 | octyl | COO⁻ | H | CH$_3$ | H | H | C=O | 2.16 ± 0.01 | 7.68 ± 2.41 |
| 5916 | Ph(CH$_2$)$_3$CH$_2$O | COO⁻ | H | H | H | H | C=O | 140 | ND |
| 5917 | Ph(CH$_2$)$_4$CH$_2$O | COO⁻ | H | H | H | H | C=O | 11.7 ± 3.2 | ND |
| 5924 | hexyl | COO⁻ | H | CH$_3$ | H | H | C=O | >600 | 24.5 |
| 5928 | octyl | NO$_2$ | H | H | H | H | C=O | >600 | ND |
| 5929 | octyl | SO$_2$NH$_2$ | H | H | H | H | C=O | 259.1 ± 24.6 | ND |
| 5932 | octyl | COO⁻ | F | H | H | H | C=O | 11.1 ± 1.1 | 13.24 ± 0.46 |
| 5934 | octyl | COO⁻ | H | OH | H | H | C=O | 29.62 | 11.75 |
| 5935 | octyl | COO⁻ | H | OCH$_3$ | H | H | C=O | 5.89 ± 1.25 | 13.6 ± 6.3 |
| 5936 | octyl | B(OH)$_2$ | H | H | H | H | C=O | >600 | ND |
| 5937 | octyl | COO⁻ | H | H | CH$_3$ | H | C=O | 3.99 ± 2.3 | 7.42 ± 1.89 |
| 5938 | octyl | COO⁻ | F | H | F | H | C=O | 30.6 ± 3.2 | 39.7 |
| 5939 | octyl | COO⁻ | NO$_2$ | H | H | H | C=O | 6.05 ± 1.9 | 9.96 ± 1.52 |
| 5940 | hexyl | PO$_4$ | H | H | H | H | C=O | >600 | ND |
| 5943 | hexyl | OH | H | H | H | H | C=O | >600 | ND |
| 5944 | octyl | H | OH | H | H | H | C=O | >600? | ND |
| 5945 | octyl | COO⁻ | CF$_3$ | H | H | H | C=O | 29.36 ± 8.2 | 22.86 ± 3.62 |
| 5946 | octyl | COO⁻ | OH | H | H | H | C=O | 7.92 ± 2.9 | 12.12 ± 5.06 |
| 5948 | octyl | COO⁻ | H | H | H | OH | C=O | 12.03 ± 2.7 | ND |
| 5949 | octyl | COO⁻ | Cl | H | H | H | C=O | 25.3 ± 3.4 | ND |
| 5950 | octyl | COO⁻ | OCH$_3$ | H | H | H | C=O | 29.6 ± 3.4 | ND |
| 5951 | octyl | H | PO$_4$ | H | H | H | C=O | 98.3 ± 2.4 | ND |
| 5953 | octyl | COO⁻ | H | H | H | H | CH$_2$ | 9.57 ± 2.03 | ND |
| 5955 | octyl | N | PO$_4$ | H | H | H | CH$_2$ | >600 | ND |
| 5961 | octyl | COO⁻ | H | CH$_3$ | H | H | CH$_2$ | >600 | 156.7 |
| 5971 | octyl | COO⁻ | H | H | CH$_3$ | H | CH$_2$ | 21.69 ± 2.8 | ND |
| 5972 | octyl | COO⁻ | H | H | H | CH$_2$CH$_3$ | CH$_2$ | 117.5 ± 3.11 | ND |
| 5973 | octyl | COO⁻ | F | H | H | H | CH$_2$ | 18.8 ± 3.31 | ND |
| 5974 | octyl | H | CH$_2$CH$_3$ | H | H | H | CH$_2$ | >600 | ND |
| 5999 | Ph(CH$_2$)$_7$ | COO⁻ | H | H | H | H | C=O | >600 | ND |
| 6037 | dodecyl | COO⁻ | H | H | H | H | C=O | 5.97 ± 0.38 | 1.99 ± 0.69 |

FIG. 1

> *PBD Inhibitor Lead Identification profile*
>
> PLK1 PBD inhibtion $IC_{50}$ < 0.50 μM, PLK2, 3, 4 PBD inhibition $IC_{50}$ > 50 μM
> Off target (related protein kinases) $IC_{50}$ > 50 μM
> Synthetic feasibility, at least 2 points of diversity, preferably no chiral centres
> No obvious toxicophores or metabolic liabilities
> Good SAR over 3 logs of potency
> MW < 550, ClogP < 5, Aqueous solubility > 10 μM
> Microsomal stability (T ½ > 40 minutes)
> Plasma protein binding <97%
> Antitumor cell killing efficacy (PLK1 overexpressing cells; avg $IC_{50}$ < 1 μM), two logs less potent on normal cells.
> apoptosis induction at $IC_{50}$ dose @ 48 hr treatment
> G2/M arrest by flow cytometry/absence of G1 arrest (PLK3)
> Decreased localization of PLK1 by microscopy

FIG. 4

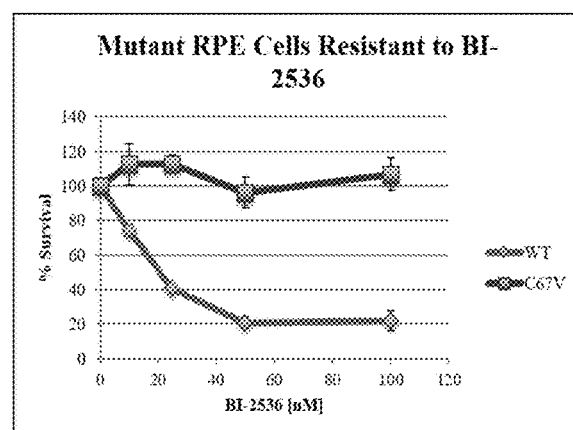
FIG. 6
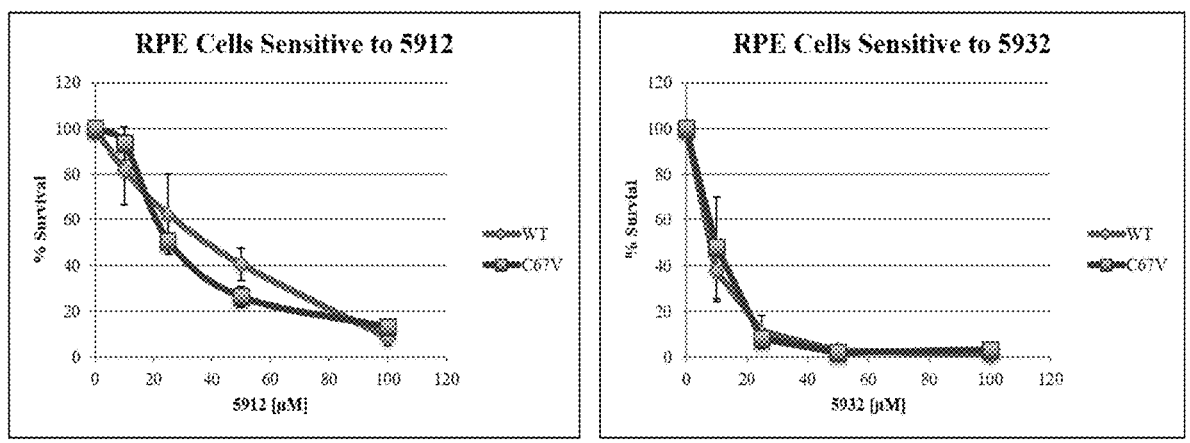
FIG. 7
FIG. 8

SEQUENCE LISTING

```
Sequence total quantity: 2
SEQ ID NO: 1            moltype = AA  length = 15
FEATURE                 Location/Qualifiers
source                  1..15
                        mol_type = protein
                        organism = synthetic construct
                        note = Description of Artificial Sequence: Synthetic peptide
SITE                    8
                        note = MOD_RES - Phosphorylated threonine
SEQUENCE: 1
MAGPMQSTPL NGAKK                                                             15

SEQ ID NO: 2            moltype = AA  length = 11
FEATURE                 Location/Qualifiers
source                  1..11
                        mol_type = protein
                        organism = synthetic construct
                        note = Description of Artificial Sequence: Synthetic peptide
SITE                    7
                        note = MOD_RES - Phosphorylated threonine
SEQUENCE: 2
GPLATSTPKN G                                                                 11
```

SMALL MOLECULE INHIBITORS SELECTIVE FOR POLO-LIKE KINASE PROTEIN

CROSS REFERENCE TO RELATED APPLICATION

This application is a continuation application of U.S. patent application Ser. No. 17/001,167, having a filing date of Aug. 24, 2020, which application is a continuation application of U.S. patent application Ser. No. 15/479,373, having a filing date of Apr. 5, 2017, which claims filing benefit of U.S. Provisional Patent Application Ser. No. 62/318,439, having a filing date of Apr. 5, 2016, all of which are incorporated herein by reference for all purposes.

SEQUENCE LISTING

The instant application contains a Sequence Listing which has been submitted electronically in XML format and is hereby incorporated by reference in its entirety. Said XML copy, created on Mar. 2, 2023, is named USC-471-CON2_881_SL.xml and is 4,011 bytes in size.

BACKGROUND

The family of polo-like kinase (PLK) proteins are central players in regulating entry into and progression through mitosis. The four known human PLKs have non-redundant and non-overlapping functions. A significant body of literature has validated PLKs as anti-tumor drug targets. For instance, profound anti-proliferative activity can be achieved through selective inhibition of PLK1 functions. Over-expression of PLK1 is frequently observed in various cancers and PLK1 expression is a prognostic indicator for outcome of patients suffering from various tumors. For example, more than half of prostate cancers over express PLK1 and this expression is positively correlated with tumor grade.

The therapeutic rationale for PLK inhibition has been validated through studies with PLK1-specific antisense oligonucleotides and has been shown to profoundly inhibit cancer cell growth in vitro and in vivo while having little effect on the proliferation of normal cells. Several studies also suggest that lethality of PLK1 against cells with mutations in p53, KRAS, and PTEN can be exploited to selectively kill tumor cells, and this research provides additional target validation. Numerous inhibitors that target ATP binding to PLKs are being clinically evaluated. Published results suggest acceptable toxicity profiles, thus warranting further investigation and the phase II trials underway. Through such research, a small molecule PLK1 inhibitor BI6727 (volasertib) was granted breakthrough status after significant benefit was observed in treating Acute Myeloid Leukemia.

Unfortunately, despite clinical progress, there are significant drawbacks for PLK inhibitors that target the ATP cleft. For instance, all ATP competitive protein kinase inhibitors suffer from the well-known concerns of relative non-specificity in the human kinome and of having to compete against high intracellular ATP concentrations. Moreover, even if ATP cleft-targeted PLK inhibitors progress fully through clinical trials, recent experience with other kinase inhibitors suggests that tumor resistance will be a problem in the future. A prime example is the first clinically validated kinase inhibitor, imatinib. While this drug was a remarkable breakthrough for chronic myelogenous leukemia, point mutations in the active site of BCR-ABL were observed soon after approval, leading to clinical resistance. It took over a decade of intense research to develop ponatinib, the first FDA-approved drug effective against the T315I mutant kinase. The probability of a similar scenario with PLK1 inhibition was underscored with a recent publication showing that a single point mutation in PLK1 (C67V) confers substantial resistance to BI2536 and several other structurally unrelated and clinically evaluated ATP inhibitors while also not affecting kinase activity. In fact, such selective pressure might partially be responsible for the lack of clinical activity of BI2536 as a monotherapy despite dramatic preclinical anti-tumor activity.

Another drawback of ATP competitive compounds arises from the knowledge that three of the mammalian PLKs are inhibited equipotently by BI2536. In particular, while this compound is more selective for PLK1, it still has nanomolar activity against PLK3. Studies have shown PLK3 to be a tumor suppressor with activities that oppose those of PLK1, and several studies have provided evidence of opposing functions of PLK1 and PLK3. Thus, anti-tumor activity of ATP inhibitors against PLK1 may be diminished by concomitant inhibition of PLK3.

Accordingly, alternative approaches and effective small molecule PLK inhibitors are needed in the art. Moreover, highly selective PLK inhibitors, and in particular, highly selective PLK1 inhibitors, would be of great benefit in the art.

SUMMARY

According to one embodiment, disclosed is a non-peptidic small molecule PLK inhibitor having the general structure of:

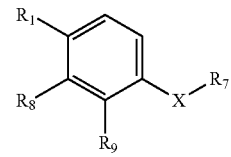

wherein $R_1$ is an alkyl, —O-alkyl, —S-alkyl, or —NH-alkyl, and optionally includes a terminal aryl;

$R_8$ and $R_9$ are independently H, alkyl, OH, $NH_2$, SH, —O-alkyl, —NH-alkyl, —S-alkyl, —CONH-alkyl, halogen, or —CN;

X is an amide, —C1 to C4 alkyl-NH—, —NH—, —SNH—, —SONH—, or —$SO_2$N—;

$R_7$ is selected from the following structures:

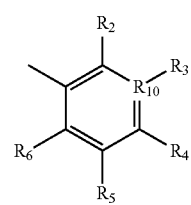

a)

in which $R_2$ through $R_6$ are independently selected from hydrogen, carboxyl, alkyl, alkyl ester, hydroxyl, methoxy, halogen, sulfonamide, phosphate, nitro, methylamine, or boronic acid, and $R_{10}$ is C or N, and $R_3$ is relevant only when $R_{10}$ is C;

b)

$R_{11}$ = CH, N c)

$R_{11}$ = CH, N d)

$R_{11}$ = CH, N e)

$R_{11}$ = CH, N f)

g)

According to another embodiment, small molecule inhibitors exhibiting selectivity for PLK1 or PLK3 are described. For instance, a PLK1 selective small molecule inhibitor is disclosed having the general structure as described above in which $R_1$ is a C3 to C8 alkyl, $R_8$ and $R_9$ are hydrogen, $R_7$ is a), $R_2$ is carboxyl, $R_3$ through $R_6$ are independently selected from hydrogen, hydroxyl, methoxy, halogen, nitro, or alkyl, $R_{10}$ is C, and X is an amide linkage.

In one embodiment, a PLK3 selective small molecule inhibitor is described. For example a PLK3 selective small molecule inhibitor can have the general structure as described above in which $R_1$ is a C6 to C12 alkyl, $R_8$ and $R_9$ are hydrogen, $R_7$ is a), $R_2$ is hydrogen or carboxyl, $R_3$ through $R_6$ are independently selected from hydrogen, carboxyl, methyl, or hydroxyl, $R_{10}$ is C, and X is an amide linkage.

In another embodiment, the PLK selective inhibitor can have the above structure wherein $R_1$ is alkyl, $R_8$ and $R_9$ are hydrogen, X is an amide linkage, and $R_7$ is one of b) through g).

BRIEF DESCRIPTION OF THE DRAWINGS

The present disclosure may be better understood with reference to the drawings, in which:

FIG. 1 is a table of exemplary inhibitors as described herein (SCCP ID numbers provided on FIG. 1 are utilized throughout this disclosure).

FIG. 4 presents a scheme for development of the small molecule inhibitors.

FIG. 6 graphically illustrates the resistance of retinal pigment epithelial (RPE) cells to BI-2536, an ATP-competitive inhibitor.

FIG. 7 graphically illustrates the sensitivity of RPE cells to an inhibitor (SCCP ID No. 5912) as disclosed herein.

FIG. 8 graphically illustrates the sensitivity of RPE cells to another inhibitor (SCCP ID No. 5932) as disclosed herein.

DETAILED DESCRIPTION

Figure 2:
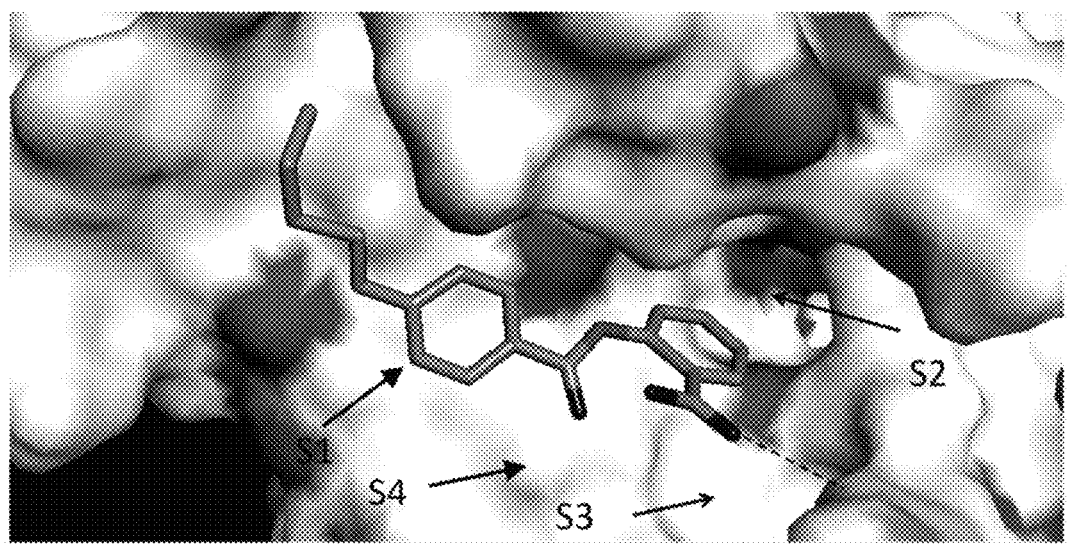
FIG. 2 illustrates the binding mode of inhibitor SCCP ID No. 5905 with the PBD of PLK1.

The following description and other modifications and variations to the presently disclosed subject matter may be practiced by those of ordinary skill in the art, without departing from the spirit and scope of the present disclosure. In addition, it should be understood that aspects of the various embodiments may be interchanged both in whole and in part. Furthermore, those of ordinary skill in the art will appreciate that the following description is by way of example only and is not intended to limit the subject matter.

The present disclosure is generally directed to small molecule PLK inhibitors that can target the polo box domain (PBD). All PLKs contain an N-terminal Ser/Thr kinase catalytic domain and a C-terminal region that includes the PBD. In the absence of a bound substrate, the PBD inhibits the basal activity of the kinase domain. Phosphorylation-dependent binding of the PBD to its ligands releases the kinase domain, while simultaneously localizing polo-like kinases to specific subcellular structures. Thus, the PBD is critical for PLK subcellular localization and substrate recognition prior to phosphorylation.

PLK1 localizes to centrosomes and kinetochores in prophase and to the spindle midzone later in mitosis, which depends on the PBD but not on its kinase activity. For instance, a PBD fragment fused with a membrane-permeable delivery peptide can cause mitotic arrest and cell death in tumor cells. Also, inducible expression of the PLK1 PBD domain fragment in PC-3 prostate cancer cells has been shown to result in significant growth inhibition, validating the concept that interfering with the PBD suppresses the proliferative effects of PLK1. Crystallography has revealed the molecular basis for PLK1 localization through the PBD and peptide inhibitors have been identified. The lack of success of HTS approaches confirms that alternative approaches to PBD inhibitor development are desirable.

The PLK inhibitors disclosed herein are small molecule inhibitors that can target the PBD. As utilized herein, the term "small molecule" refers to a non-peptidic compound that is generally about 1000 Daltons or less (i.e., atomic mass units, one Dalton being equivalent to $\frac{1}{12}$ the mass of a $^{12}C$ isotope). In other embodiments, the small molecule inhibitor may be about 500 Daltons or less, about 400 Daltons or less, or about 300 Daltons or less.

Beneficially, the small molecule PBD-targeted inhibitors can retain activity exhibited by peptidic inhibitors, e.g., antitumor activity against cancer cells, and, in one particular embodiment, can exhibit activity against cancer cells that can acquire resistance to ATP-based inhibitors. As such, in one embodiment, disclosed inhibitors can be used in combination with ATP-based inhibitors as a synergistic means of PLK1 targeting in the clinic. Moreover, by targeting non-catalytic functions, PLK can be less likely to obtain resistance to the inhibitors.

The non-peptidic inhibitors have been developed with activity and cellular phenotypes consistent with target engagement of PLK1, and, in one embodiment, can induce apoptosis. As such, the inhibitors can be useful as mechanistic probes to characterize cellular defects of blocking PLK1 independent of catalytic activity, and can be used in combination with catalytic PLK1 inhibitors as a dual approach to attacking PLK1, analogous to many successful clinical precedents (e.g., Bactrim (antibiotic), Combivir® (antiviral), pertuzumab and trastuzumab used in HER2 breast cancer).

Disclosed PBD-targeted inhibitors that are specific for PLK1 are also much less likely to affect the activity of the PLK3 tumor suppressor, as certain of the PLK1 PBD domain inhibitors have minimal activity against PLK3, as discussed further herein.

The small molecule inhibitors can exhibit comparable affinity to peptidic PBD inhibitors and can possess anti-proliferative phenotypes in cells consistent with the observed decrease in PLK1 centrosomal localization. The inhibitors can demonstrate evidence of enhanced PLK1 inhibition in cells relative to peptides and can induce monopolar and multipolar spindles, in contrast to previously reported small molecule PBD inhibitors that display phenotypes only partially representative of PLK1 knockdown. The inhibitors can function as isotype, kinase-selective, non-ATP competitive inhibitors and can be utilized as PLK1 selective anti-tumor therapeutics.

The small molecule inhibitors described herein include an alkyl benzamido benzoic acid core structure that has been utilized to build the PBD inhibitors with high potency and selectivity. As utilized herein, unless otherwise noted, the term "alkyl" refers to any straight-chain or branched, substituted or unsubstituted C1 to C20 alkyl group.

In one embodiment, a non-peptidic small molecule PLK inhibitor can have the general structure of:

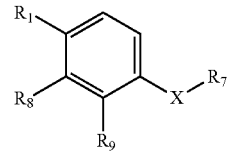

wherein

R$_1$ comprises an alkyl, —O-alkyl, —S-alkyl (e.g., —S—CH$_3$), or —NH-alkyl, and optionally includes a terminal aryl;

R$_8$ and R$_9$ are independently hydrogen, alkyl, OH, NH$_2$, SH, —O-alkyl, —NH-alkyl, —S-alkyl, —CONN-alkyl, halogen, or —CN;

X is an amide (i.e., either —C═O—NH— or —NH—C═O—), —C1 to C4 alkyl-NH—, —NH—, —SNH—, —SONH—, or —SO$_2$N—;

R$_7$ is selected from the following structures:

a)

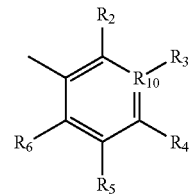

in which R$_2$ through R$_6$ are independently selected from hydrogen, carboxyl, alkyl, alkyl ester, hydroxyl, methoxy, halogen, sulfonamide, phosphate, nitro, methylamine, or boronic acid, and R$_{10}$ is C or N, and R$_3$ is relevant only when R$_{10}$ is C;

b)

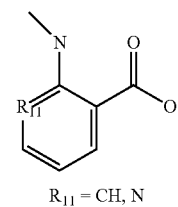

R$_{11}$ = CH, N c)

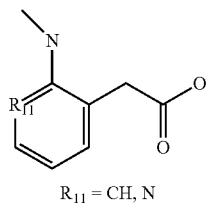

R$_{11}$ = CH, N

-continued d)

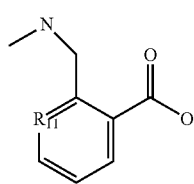

$R_{11}$ = CH, N e)

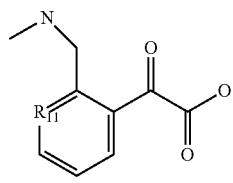

$R_{11}$ = CH, N f)

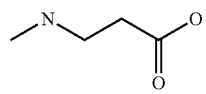

g)

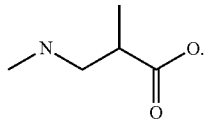

For example, in one embodiment, the small molecule inhibitors can have the general structure of:

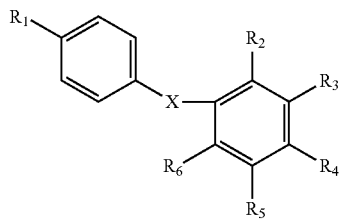

wherein $R_1$ comprises an alkyl, —O-alkyl, —S-alkyl, or —NH-alkyl, and optionally includes a terminal aryl;

$R_2$ through $R_6$ are independently selected from hydrogen, carboxyl, alkyl, alkyl ester, hydroxyl, methoxy, halogen, sulfonamide, phosphate, nitro, methylamine or boronic acid; and X is an amide, —C1 to C4 alkyl-NH—, —NH—, —SNH—, —SONH—, or —SO$_2$N—.

FIG. 1 presents the structure, structure activity relationship (SAR) and interaction data of several representative small molecule inhibitors of this embodiment. A clear SAR for substituents at the 4 position of increasing alkyl chain length has been established and provides a solid basis and rationale for improvements in potency.

In another embodiment, the small molecule inhibitors can have the general structure of:

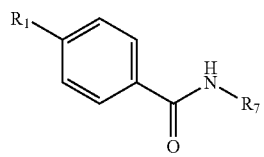

wherein $R_1$ comprises an alkyl, —O-alkyl, —S-alkyl, or —NH-alkyl, and optionally includes a terminal aryl;

$R_7$ is selected from:

b)

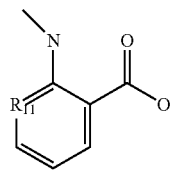

$R_{11}$ = CH, N c)

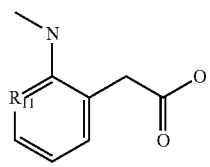

$R_{11}$ = CH, N d)

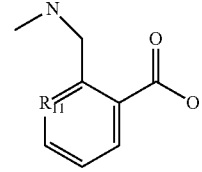

$R_{11}$ = CH, N e)

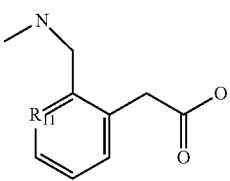

$R_{11}$ = CH, N f)

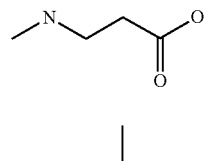

g)

Table 1, below, below presents the structure of several representative PLK inhibitors of this embodiment.

TABLE 1

| SCCP ID No. | $R_1$ | X | $R_7$ | PLK1 PBD $IC_{50}$ (µM) |
|---|---|---|---|---|
| 5992 | octyl | amide | b), $R_{11}$ = N | ND |
| 5904 | hexyl | amide | b), $R_{11}$ = N | >600 |
| 5913 | octyl | amide | d), $R_{11}$ = CH | 105 |
| 5975 | octyl | amide | f) | >200 |
| 5976 | octyl | amide | g) | 343-450 |
| 5997 | octyl | amide | c), $R_{11}$ = CH | ND |

FIG. 2 schematically illustrates the binding mode of one representative inhibitor (SCCP ID No. 5905 of FIG. 1) with the PBD of PLK1. The interaction of the carboxylate at $R_2$ with the phosphate binding site is shown by the dashed line. The unoccupied regions that can be exploited to improve the inhibitor affinity further are indicated in FIG. 2 by the S1-S4 labels. The SAR and predicted interactions of the hydrophobic slot in the PBD (FIG. 2) indicates that linear alkyl groups can result in an enhancement in potency. As indicated in FIG. 1, synthesis of the 4 substituted analogs, including n-propyl, butyl, hexyl, and octyl groups, led to improved potencies.

The alkyl benzamido benzoic acid core provides a scaffold that exhibits excellent drug development potential. The small molecule inhibitors have relatively low molecular weight, possess high ligand efficiency, have a low polar surface area (e.g., about 200 Å$^2$ or less, about 100 Å$^2$ or less, or about 75 Å$^2$ or less in some embodiments, e.g., 66 Å$^2$ for SCCP ID No. 5912) and can have a ClogP of about 5. In addition, they are relatively simple to synthesize by standard chemical practice (examples of which are described further herein and have considerable scope for high activity through expansion of the molecules into unoccupied regions of the PBD groove (FIG. 2)).

The small molecule inhibitors can be designed to exhibit PLK selectivity and/or predetermined activity. By way of example, SCCP ID No. 5881 (FIG. 1) has low micromolar activity in the binding assay and possesses a 4-hexylbenzamide and 2-aminobenzoic acid bonded with an amide linkage. Modeling with the PBD of PLK1 has illustrated that the ortho-carboxylic acid is a bioisostere for the phosphate group in the peptide context. A number of variants of SCCP ID No. 5881 have been synthesized and the SAR examined, with results provided in FIG. 1. As shown, movement of the carboxylate to the $R_3$ position substantially decreased the activity (SCCP ID No. 5903).

SAR can be predetermined in one embodiment by varying the length of the alkyl chain at the $R_3$ location. For example, decreasing the length can reduce binding potency whereas increasing it can increase binding potency. For example, increasing the length of the alkyl chain to 8 carbons (e.g., SCCP ID No. 5912) and to 12 carbons (e.g., SCCP ID No. 6037) resulted in notable increases in binding activity relative to SCCP ID No. 5881.

The inhibitors can include a halogen moiety at one or more of the $R_2$ through $R_6$ locales. For example, an $R_6$-fluoro derivative was synthesized (SCCP ID No. 5932) and shown to have similar activity relative to SCCP ID No. 5912.

The inhibitors can include an alkyl moiety at one or more of the $R_2$ through $R_6$ locales, which can be utilized to provide predetermined activity and/or selectivity. For example, addition of a methyl group at the $R_5$ position of the benzoic acid ring (SCCP ID No. 5915) resulted in an almost 5-fold increase in activity for PLK1 as compared to SCCP ID No. 5912, whereas a methyl group at $R_4$ (SCCP ID No. 5937) provided lower PLK1 activity.

In some embodiments, the disclosed inhibitors can discriminate between PLK family members. Beneficially, the inhibitors can replicate a PLK1 phenotype in contrast to the partial phenotype obtained with PBD dominant negative and small molecule inhibitors utilized in the past. Thus, it is believed that inhibitors formed, as described herein, can inhibit both subcellular localization and substrate phosphorylation.

As illustrated in FIG. 1, the small molecule inhibitors can be designed to exhibit preferential specificity between PLK1 and PLK3. For example, structures that include a simple benzoic acid moiety can possess less specificity for PLK1 versus PLK3. However, other compounds, such as SCCP ID No. 5915, with a methyl group at $R_4$, exhibit a high selectivity for PLK1. SCCP ID No. 5912, with an $R_1$ octyl substituent is relatively equipotent for PLK1 and PLK3 PBD binding, whereas SCCP ID No. 6037 with an $R_1$ dodecyl group shows selectivity for PLK3.

Without wishing to be bound to any particular theory, it is believed that interactions with the unoccupied hydrophobic pocket (FIG. 2, S3), through derivatization at the $R_4$ and $R_5$ positions of the inhibitor structure, can lead to the high PLK1 vs. PLK3 selectivity. By way of example, a small molecule inhibitor exhibiting high PLK1 selectivity can have the following general structure:

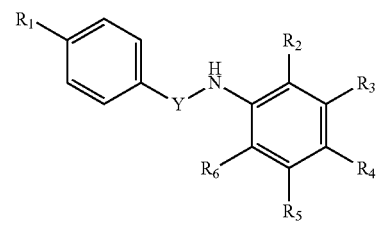

wherein
  $R_1$ comprises a C3 to C8 alkyl or —O—C3 to C8 alkyl and optionally includes a terminal aryl;
  $R_2$ is carboxyl;
  $R_3$ through $R_6$ are independently selected from hydrogen, hydroxyl, methoxy, halogen, or alkyl;
  Y is a C=O (i.e., an amide linkage).

In one particular embodiment, a PLK1 selective small molecule inhibitor can have the above structure in which $R_3$ and $R_6$ are hydrogen and $R_4$ and $R_5$ are independently selected from hydrogen, hydroxyl, methoxy, halogen or alkyl, wherein at least one of $R_4$ and $R_5$ is not hydrogen.

In another embodiment, the small molecule inhibitor can be selective for PLK3. For example, a PLK3 selective small molecule inhibitor can have the general structure of:

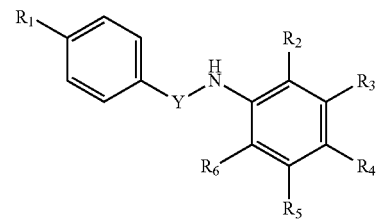

wherein
R$_1$ comprises a C6 to C12 alkyl;
R$_2$ is hydrogen or carboxyl;
R$_3$ through R$_6$ are independently selected from hydrogen, carboxyl, methyl, or hydroxyl; and
Y is a C=O (i.e., an amide linkage).

In one embodiment, a PLK3 selective inhibitor can have the above structure in which R$_3$ through R$_6$ are hydrogen and optionally, the R$_1$ group can be a C12 alkyl chain (e.g., SCCP ID No. 6037).

Figure 3:
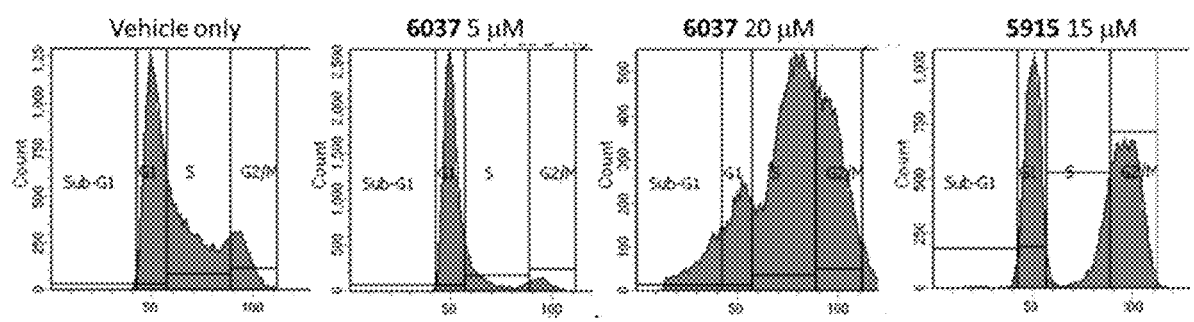
FIG. 3 illustrates the dose dependent G2/M arrest induced by two of the inhibitors (SCCP ID Nos. 5915 and 6037) of Table 1.

PLK specificity can be useful in therapeutic applications, as well as in research-oriented application. For example, a differential cell cycle effect has been observed dependent on the selectivity (PLK1 vs. PLK3) of the inhibitor, and this effect has moreover been observed to be dose dependent. Untreated cells can progress through one cell cycle and begin transit through a second cycle (47% G1 and 37% S phase by DAPI, 62% positive for BrdU labeling, demonstrating a majority of the cells are actively replicating early in S phase). As shown in FIG. 3, cells treated with SCCP ID No. 6037 (PLK3 selective) at 5 μM revealed a profound block in G1 after progressing through one mitosis (FIG. 3, $2^{nd}$ panel: 77% G1 and 15% S by DAPI, only 27% BrdU+). Release into a higher dose of 20 μM, SCCP ID No. 6037 resulted in a significant block prior to mitosis (FIG. 3, $3^{rd}$ panel; 28% G2/M by DAPI, compared to 13% for vehicle and 7% for 5 μM, SCCP ID No. 6037). In contrast, release of PC3 cells in SCCP ID No. 5915 (PLK1 selective), resulted in a clear G2/M accumulation (FIG. 3, $4^{th}$ panel; 42% G2/M by DAPI, and only 13% of the cells BrdU+).

These results are completely consistent with the fact that at the lower dose of SCCP ID No. 6037, insufficient PLK1 inhibition results in the cells entering mitosis, dividing, and then arresting in G1 where PLK3 inhibition prevents entry into S phase. At the higher dose, PLK1 is inhibited as the cells exit from S phase and then accumulate in G2/M. The putative PLK3-dependent G1 arrest was only revealed at a lower dose at which PLK1 inhibition is not predominating. Thus, the disclosed PLK selective inhibitors can provide a route for study and understanding of cell cycles, and the disclosed PLK selective inhibitors can function as a chemical probe useful in mechanism of action studies.

Disclosed small molecule inhibitors can also encourage apoptosis. For instance, cell cycle analysis and a caspase apoptosis assay have indicated high levels of apoptosis for SCCP ID No. 6037 and SCCP ID No. 5915 in contrast to virtually none for the negative control SCCP ID No. 5914, suggestive of target engagement for the small molecule inhibitors.

The small molecule inhibitors can be developed and synthesized according to methods as are generally known in the art. For instance, in one embodiment, an iterative combinatorial method can be utilized as described in U.S. Pat. No. 9,175,357 to McInnes, et al., which is incorporated herein by reference. Overall, this combinatorial approach is based upon a known peptide inhibitor and allows both regions of the inhibitor molecule (i.e., the N-cap and the C-cap) to be optimized independently to maximize the affinity and drug-likeness of each component. FIG. 4 provides a general scheme for synthesis according to this particular embodiment. Peptide inhibitors that can be utilized as the basis for development of the small molecule inhibitors can include any peptide inhibitor capable of selectively inhibiting PLK. For instance, the basis peptide inhibitor can include both native peptides and variants thereof.

Figure 5:
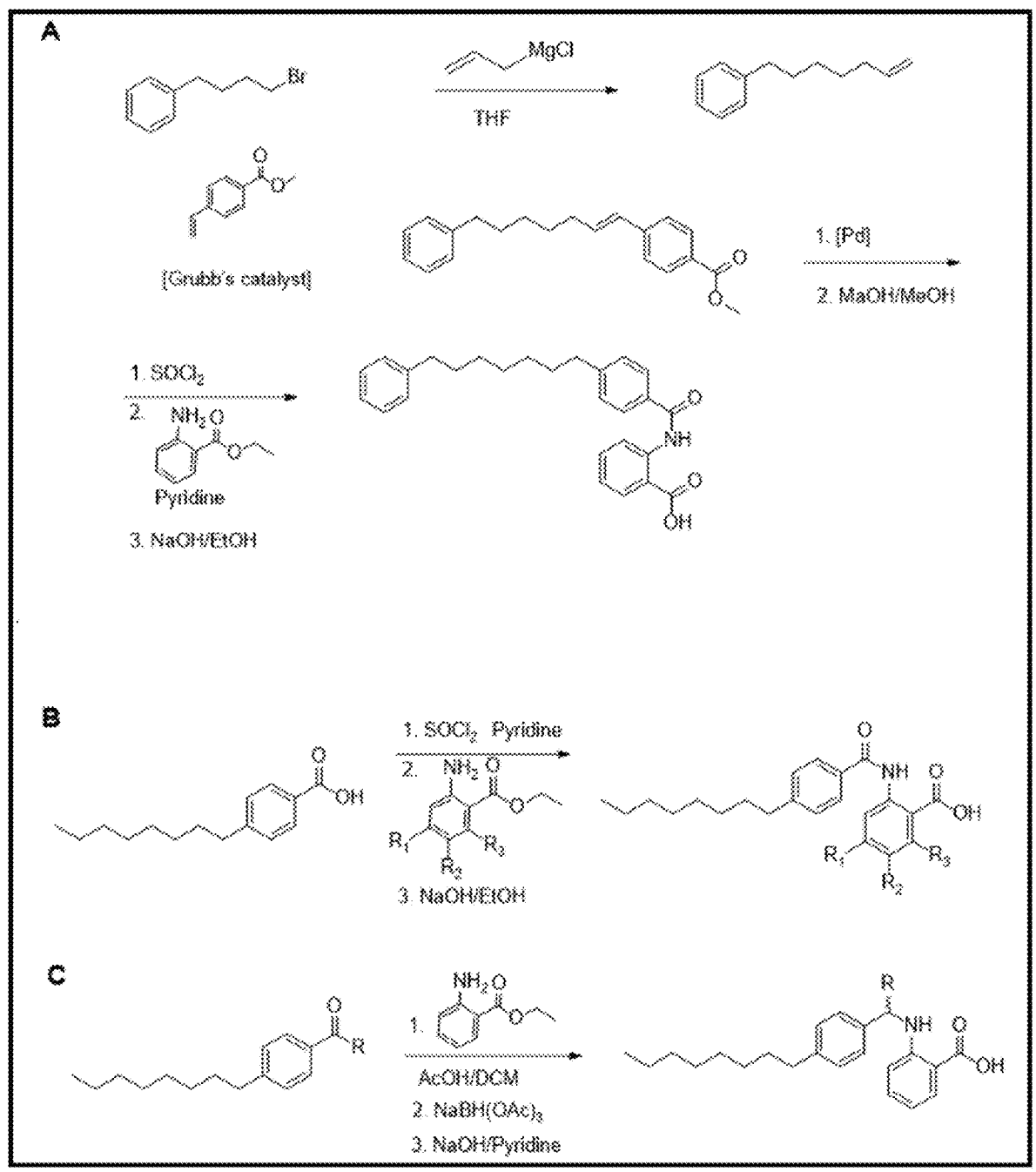
FIG. 5 presents exemplary synthesis schemes for formation of the inhibitors.

Synthesis of the inhibitors can be carried out according to any suitable chemical process. By way of example, and without limitation, FIG. 5 provides three possible schemes for inhibitors: 1) FIG. 5; 2) scheme A presents a methodology for incorporating aryl groups onto the linker; and 3) scheme B presents one methodology for derivatization of the inhibitor at the R$_4$ and R$_5$ positions of the above described structures (R$_1$, R$_2$, on scheme B). This scheme can also be utilized to modulate the R$_2$ position (e.g., an R$_2$ carboxylate in the above described structures) by addition of electron withdrawing groups and replacement with, e.g., phosphate isosteres.

A benefit of the iterative combinatorial formation approach is the modularity in identification of desired moieties for each subsite. The desired fragments can be combinatorially ligated so that essential compound features will not be compromised during the linking process. The individual fragments can be optimized for potency and drug-like properties and then linked to improve pharmacodynamic and pharmacokinetic properties. This lead optimization stage can be informed by cellular assays and detailed mechanistic studies of anti-tumor effects of the inhibitors. The modularity and combinatorial aspects of this method can allow for the moieties to be exchanged and more narrowly target the characteristics of the physicochemical characteristics, as well as minimize metabolic or toxicophore liabilities, with particularly preferred characteristics depending primarily on the application of the inhibitor (e.g., research, in vivo).

According to one embodiment, following identification and optimization of the end groups, a bridging strategy between the benzamido moiety and an aminobenzoic acid moiety can be selected. For instance, the bridge between the aryl groups can include an amide, ether, thioether, amine, or carbon-carbon linkages.

The fragments can be subdivided into chemotypes appropriate for docking into the particular PBD sub-sites and prioritized using pharmacophore features to select fragments with desired functionality. High-throughput docking of virtual libraries into the PBD binding site can be performed during the synthesis process. High-throughput docking (HTD) can then be used in refinement of the fragments with calculations including more accurate scoring functions, and interactions filters to limit fragments to those containing the geometrically appropriate functionality. HTD programs such as, without limitation, LIDAEUS, LigandFit, Accelryse®, and Glide (SchröDinger®), can incorporate the desired enhancements and can be used to dock virtual fragment libraries into each site. For example, when calculations are parallelized, 100,000 fragments can be screened between 5 and 50 hours depending on the parameterization and number of CPU's employed. Due to inherent inaccuracies with docking, it can be expedient to use different implementations to minimize errors, biases, or incorrect parameters of a single synthesis process. A balance of electrostatic, van der Waals, and H-bonding interactions between each fragment and the binding groove can be used to form the inhibitor having the desired characteristics.

After development of the inhibitor fragments from identified chemotypes, these can be combined in order to substitute all peptidic determinants and form the non-peptidic small molecule inhibitors. Optimization of the fragments can be facilitated using 3-D structures generated through crystallography and flexible molecular docking (using, e.g., Cdocker, Accelrys®, etc.) to predict favorable interactions of modified compounds and improve complementarity.

The present disclosure may be better understood with reference to the Examples, set forth below.

EXAMPLE 1

Materials and Methods

Fluorescence Polarization Assay

Materials were dissolved in DMSO (10 mM) and diluted from 10 nM to 600 µM (maximum of 6% DMSO tolerance in the assay). PLK1 PBD (367-603) and PLK3 PBD (335-646) proteins were obtained from BPS Biosciences Inc. (San Diego, CA); 17 ng PLK1 and 156 ng PLK3 were used per reaction. The fluorescein-tracer phospho-peptides (MAGPMQS[pT]PLNGAKK (SEQ ID NO: 1) for PLK1, and GPLATS[pT]PKNG (SEQ ID NO: 2) for PLK3) were used at a final concentration of 10 nM. Incubation was carried out at room temperature for 45 minutes. Fluorescence was measured using a DTX 880 plate reader and Multimode Analysis software (Beckman Coulter, Brea, CA). The polarization values in millipolarization (mP) units were measured at an excitation wavelength of 488 nm and an emission wavelength of 535 nm. Each data point was performed in triplicate for every experiment, and experiments were performed at least three times. An $IC_{50}$ value for each compound was calculated from linear regression analysis of the plots.

PLK1 Kinase Inhibition Assay

The CycLex® Polo-like Kinase 1 Assay/Inhibitor Screening Kit was used to measure catalytic inhibition (MBL Life Science, Nagano, Japan). This ELISA assay measures the catalytic activity of full length PLK1 for a defined substrate, which is detected by an anti-phospho-threonine antibody (PPT-07) and peroxidase coupled secondary antibody. Plates pre-coated with a Threonine-containing substrate were incubated with PLK1, kinase buffer containing 7.5 µM ATP (modification from recommended concentration), in the absence or presence of increasing concentration of inhibitor. After incubation, the phosphorylated substrate resulting from PLK1 kinase activity was detected using the PPT-07 antibody and horseradish peroxidase conjugated anti-rabbit IgG antibody. Peroxidase catalyzes the conversion of the colorless solution to yellow, which was quantified using a DTX 880 plate reader. Absorbance measurements (450 nm) were plotted to calculate activity in each sample, and % inhibition was calculated in the wells relative to activity in the absence of inhibitor.

Cell Culture

HeLa cervical cancer cells were obtained from ATCC (Manassas, VA). Histone H2B GFP-labeled HeLa cells (HeLa-H2B-GFP) were kindly provided by Dr. Geoffrey Wahl (Gene Expression Laboratory, Salk Institute), and were confirmed as >95% GFP positive by FACS (data not shown) but were not otherwise authenticated. Cells were maintained in DMEM (Invitrogen™, Carlsbad, CA) supplemented with 10% FBS or Corning® Nu-serum™ (BD™ Biosciences, Franklin Lakes, NJ) and 1% penicillin/streptomycin (Invitrogen™) in a humidified incubator and 5% $CO_2$ at 37° C.

PC3 prostate cancer cells were maintained in DMEM (Invitrogen™, Carlsbad, CA) supplemented with 10% FBS or Corning® Nu-serum™ (BD™ Biosciences, Franklin Lakes, NJ) and 1% penicillin/streptomycin (Invitrogen™) in a humidified incubator and 5% $CO_2$ at 37° C.

A-549 lung cancer cells were maintained in Hams F-12 1× with glutamine (Corning® Cellgro, Manassas, VA), and supplemented with 10% FBS or Corning® Nu-serum™ (BD™ Biosciences, Franklin Lakes, NJ) and 1% penicillin/streptomycin (Invitrogen™) in a humidified incubator and 5% $CO_2$ at 37° C.

HCT-116 (p53 +/+ and −/−) colon cancer cells were maintained DMEM (Invitrogen™, Carlsbad, CA) supplemented with 10% FBS or Nu-serum (BD™ Biosciences, Franklin Lakes, NJ) and 1% penicillin/streptomycin (Invitrogen™) in a humidified incubator and 5% $CO_2$ at 37° C.

Retinal Pigment Epithelial (RPE) cells were maintained in 1:1 DMEM/Hams F-12 (Invitrogen™, Carlsbad, CA; Corning® Cellgro, Manassas, VA), and supplemented with 10% FBS or Corning® Nu-serum™ (BD™ Biosciences, Franklin Lakes, NJ) and 1% penicillin/streptomycin (Invitrogen™) in a humidified incubator and 5% $CO_2$ at 37° C.

Cell Viability Assay

Exponentially growing cells were plated in 96-well dishes. Dose response curves were used to treat cells for 72 hours with inhibitors. Following the three-day treatment, cell viability was measured using the MTT (3-(4,5-dimethylthiazol-2-yl)-2,5-diphenyltetrazolium bromide) colorimetric assay. Cells were incubated for 3 hours with MTT allowing viable cells to metabolize the tetrazolium dye to a purple colored solution. Absorbance measurements (595 nm) were quantified using a DTX 880 plate reader and $IC_{50}$ values were generated for FLIPs.

Analysis of Cell Cycle Progression by FACS

Serum-Starved Synchronization

Cells were synchronized in G1 by serum starvation. Briefly, exponentially growing cells were plated overnight. Media (DMEM, 10% FBS, 1% Pen. Strep.) was then removed and replaced with media containing no FBS. Cells were starved for 72 hours then treated for 24 hours with inhibitor. Following treatment, cells were harvested and processed for endpoint experimental analysis.

BrdU Labeling/FACS

Ethanol fixative was removed by centrifugation and the cells were washed with 1 mL ice-cold PBS/1% BSA. Cells were denatured by resuspending in 0.2 mg/mL pepsin in 2N HCl and incubated in 37° C. water bath for 15 minutes. Hydrolysis was then terminated by adding 1 M Invitrogen™ Novex® Tris-Glycine. Cells were then washed with PBS/1% BSA then the primary anti-BrdU antibody (1:100 dilution in TBFP; 0.5% Tween-20, 1% BSA, 1% FBS, PBS) was added and cells were incubated for 25 minutes in the dark, at room temperature. Cells were subsequently washed with PBS/1% BSA then allowed to incubate for 25 minutes in the secondary fluorescent antibody (1:200 dilution Alexa Fluor® 488 F(ab')₂ fragment of goat anti-mouse IgG). Cells were washed once more with PBS/1% BSA and re-suspended in DAPI for 30 minutes before being analyzed by flow cytometry.

EXAMPLE 2

PBD-Inhibitors Bind Potently to the PLK1-PBD and are Selective

Substructure searching for 4-alkybenzamide derivatives in commercial libraries and subsequent testing identified one lead molecule inhibitor, SCCP ID No: 5881. From this lead, the structure activity relationship (SAR) of more than forty small molecules was analyzed. The total of these compounds can be found in FIG. 1. Specifically, compound binding to PLK1 (discussed first) and PLK3 (discussed second) in vitro was analyzed. ATP inhibition was also measured and compound activity analyzed in cancer cells.

Structure Activity Relationship of C-capping Group on Benzamide Small Molecules

SCCP ID No: 5880 (butyl-benzamide) did not bind to the PBD of PLK1, however SCCP ID No: 5905 (pentyl-benzamide) bound to the PLK1 PBD with weak affinity ($IC_{50}$=223.6±4.88 µM). When the alkyl tail length was increased from pentyl to hexyl PLK1 binding increased. For instance, for SCCP ID No: 5881, binding increased about 12-fold ($IC_{50}$=18.4±5.3 µM). SCCP ID No: 5881 also bonded to PLK3 ($IC_{50}$=18.04±5.18 µM) but remained 5-fold selective for PLK1. An increase in binding for PLK1 was seen by further lengthening (octyl) the alkyl tail (e.g., SCCP ID No: 5912) ($IC_{50}$=11.27±2.7 µM). Selectivity was also marginally improved (PLK3 $IC_{50}$=15.48±0.01 µM), relative to SCCP ID No: 5881. Further lengthening of the alkyl tail was carried out to determine if PLK1 binding would be further increased. Increasing the carbon chain to 12 carbons resulted in the generation of the least selective small molecule SCCP ID No: 6037 (PLK1 $IC_{50}$=5.97±0.38; PLK3 $IC_{50}$=1.99±0.69; Fold=1.6) as shown in Table 2, below.

TABLE 2

| SCCP ID No. | PLK1 $IC_{50}$ (µM) | PLK3 $IC_{50}$ (µM) | Selectivity Fold Index | PLK1 Kinase Inhibitory Act. $IC_{50}$ (µM) |
| --- | --- | --- | --- | --- |
| 5880 | >600 | ND | ND | ND |
| 5905 | 223.6 ± 4.88 | ND | ND | ND |
| 5881 | 18.4 ± 5.3 | 18.04 ± 5.18 | 5 | ND |
| 5912 | 11.27 ± 2.7 | 15.48 ± 0.01 | 6.9 | 42.36 |
| 6037 | 5.97 ± 0.38 | 1.99 ± 0.69 | 1.6 | ND |

Several of the inhibitors were examined upon variation on the C-terminal fragment. Results are provided in Table 3, below. When the position of the carboxylic acid was moved from ortho to meta (from the alanine), a loss of PLK1 binding affinity was observed (SCCP ID No: 5903 $IC_{50}$=129.8±3.6 µM) with minimal selectivity (PLK3 $IC_{50}$=43.62±1.69 µM). No binding was observed with a sulfonamide phospho-mimic (SCCP ID No: 5908), or when using a phosphate (SCCP ID No: 5940) or hydroxyl (SCCP ID No: 5943) group. Interestingly, when a methyl group was positioned meta to the carboxylic acid (SCCP ID No: 5924), PLK3 PBD binding was observed ($IC_{50}$=24.5 µM), but no binding to PLK1.

TABLE 3

| SCCP ID No: | PLK1 $IC_{50}$ (µM) | PLK3 $IC_{50}$ (µM) | Selectivity Fold Index |
| --- | --- | --- | --- |
| 5881 | 18.4 ± 5.3 | 18.04 ± 5.18 | 5 |
| 5903 | 129.8 ± 3.6 | 43.62 ± 1.69 | 1.6 |
| 5908 | >600 | ND | ND |
| 5924 | >600 | 24.5 | ND |
| 5940 | >600 | ND | ND |
| 5943 | >600 | ND | ND |

Several derivatives of the octyl-containing SCCP ID No: 5912 were synthesized and an analysis of the SAR of substituents on the C-terminal replacement was analyzed. As shown in Table 4, below as expected due to the putative contribution of the negatively charged carboxylate group, PLK1 binding was lost when the carboxylic acid was converted to a ethyl ester (SCCP ID No: 5914; $IC_{50}$=>600 µM). This compound was then used as a negative control for cellular analysis.

TABLE 4

| SCCP ID No: | PLK1 $IC_{50}$ (µM) | PLK3 $IC_{50}$ (µM) | Selectivity Fold Index | PLK1 Kinase Inhibitory Act. $IC_{50}$ (µM) |
| --- | --- | --- | --- | --- |
| 5912 | 11.27 ± 2.7 | 15.48 ± .01 | 6.9 | 42.36 |
| 5914 | >600 | ND | ND | ND |
| 5932 | 11.1 ± 1.1 | 13.24 ± 0.46 | 6 | 48.9 |
| 5915 | 2.16 ± 0.01 | 7.68 ± 2.41 | 17.8 | 24.3 |
| 5937 | 3.99 ± 2.3 | 7.42 ± 1.89 | 9.3 | ND |

When SCCP ID No: 5932 (Table 4) was synthesized containing a fluorine ortho to the carboxylic acid, PLK1 PBD binding affinity did not improve (relative to SCCP ID No: 5912, Table 4), nor was PLK1 selectivity increased. When fluorine was added at both the ortho and para positions (SCCP ID No: 5938, Table 5), PLK1 PBD binding decreased ($IC_{50}$=30.6±3.2 µM) as did PLK3 binding ($IC_{50}$=39.7 µM).

TABLE 5

| SCCP ID No: | PLK1 $IC_{50}$ (µM) | PLK3 $IC_{50}$ (µM) | Selectivity Fold Index |
| --- | --- | --- | --- |
| 5935 | 5.89 ± 1.25 | 13.6 ± 6.3 | 11.5 |
| 5938 | 30.6 ± 3.2 | 39.7 | 6.5 |
| 5939 | 6.05 ± 1.9 | 9.96 ± 1.52 | 8.2 |

Improved PLK1 binding ($IC_{50}$=2.16±0.01 µM) and selectivity (PLK3 $IC_{50}$=7.68±2.41 µM, Fold Selectivity=18) was observed upon addition of a methyl group meta to the carboxylic acid (SCCP ID No: 5915, Table 4). It is important to note that the only difference between this compound and SCCP ID No: 5924 (Table 3) is the length of the alkyl tail. Increasing the length from hexyl (SCCP ID No: 5924, Table 3) to octyl (SCCP ID No: 5915, Table 4) dramatically improved PLK1 binding and produced the most selective compound in this series (Table 4). When the methyl group was positioned para to the carboxylic acid (SCCP ID No: 5937, Table 4), PLK1 selectivity decreased 2-fold relative to SCCP ID No: 5915 (compare selectivity fold 18 with 9.3).

A compound containing a methoxy group positioned meta to the carboxylic acid (SCCP ID No: 5935, Table 5) was 11.5-fold selective for PLK1, binding with an $IC_{50}$=5.89±1.25 µM.

SCCP ID No: 5939 (Table 5) contains a nitro group ortho to the carboxylic acid. It is 8-fold selective for PLK1, binding to the PLK1 PBD with an $IC_{50}$=6.05±1.9 µM (PLK3 PBD $IC_{50}$=9.96±1.52 µM).

Small molecule inhibitors containing an alkyl benzamine flexible structure were also synthesized to explore the SAR of compounds with less rigidity. Results are shown in Table 6, below. For instance, SCCP ID No: 5953 was synthesized with a methylamino instead of the amide linkage found in SCCP ID No: 5912 (Table 4). Binding to PLK1 was slightly improved (SCCP ID No: 5953 $IC_{50}$=9.57±2.03), relative to SCCP ID No: 5912. Next, SCCP ID No: 5961 contains the methylamino linker and a methyl group meta to the carboxylic acid—the same substitution at the $R_4$ position as SCCP ID No: 5915 (Table 4). Binding of SCCP ID No: 5961 to the PLK1 PBD was undetectable, but it did have weak affinity for the PLK3 PBD ($IC_{50}$=156.7 µM). This suggests an important conformational role for compound binding. Positioning of a methyl group para to the carboxylic acid (e.g., SCCP ID No: 5971), resulted in improved PLK1 binding ($IC_{50}$=21.69±2.8 µM) relative to SCCP ID No: 5961. This represents more than 27-fold increase in PLK1 binding relative to SCCP ID No: 5961, however there was a 2-fold loss in binding relative to SCCP ID No: 5953. This further suggests that the conformation of the compound within the binding pocket is important for the methyl group substituent.

TABLE 6

| SCCP ID No: | PLK1 $IC_{50}$ (µM) | PLK3 $IC_{50}$ (µM) | Selectivity Fold Index |
|---|---|---|---|
| 5953 | 9.57 ± 2.03 | ND | ND |
| 5961 | >600 | 156.7 | ND |
| 5971 | 21.69 ± 2.8 | ND | ND |

The ability of the most promising compounds to inhibit the catalytic activity of PLK1 was investigated using an in vitro ELISA-based PLK1 kinase assay. The PBD-based PLK1 inhibitors (SCCP ID Nos: 5912, 5932, and 5915) inhibited the catalytic activity of the protein ($IC_{50}$=42.3 µM, 48.9 µM, and 24.3 µM, respectively) (Table 4). The results from this assay were an important confirmation of compound binding to PLK1 in an orthogonal assay.

The most promising inhibitors of FIG. 1 were tested in multiple cancer cell lines, including HeLa cervical cancer cells, PTEN deficient prostate cancer (PC3) cells, and KRAS mutant lung cancer (A-549) cells. Results are shown in Table 7, below. Each of these cancer cells lines were sensitive to the lead PBD-inhibitors in a cell viability assay, with the A-549 lung cancer cells being the most sensitive overall. This is consistent with literature stating a synthetic lethal interaction exists with PLK1 mutant RAS cancer cells. A synthetic lethal interaction has also been demonstrated between PLK1- and PTEN-deficient prostate cancer cells. A differential sensitivity was also observed depending on p53 status. Specifically, p53 null HCT 116 colon cancer cells were more sensitive to the PBD-inhibitors relative to p53 proficient HCT 116 cells.

TABLE 7

| SCCP ID No: | HeLa (µM) | PCC-3 (µM) | A-549 (µM) | HCT116 (p53 −/−) (µM) | HCT116 (p53 +/+) (µM) |
|---|---|---|---|---|---|
| 5912 | 15.2 ± 1.4 | 15.1 ± 1.7 | 2.8 ± 0.1 | 8.0 ± 1.7 | 14.8 ± 6.4 |
| 5914 | >100 | >100 | ND | ND | ND |
| 5915 | 15.5 ± 1.7 | 16.3 ± 2.1 | 5.1 ± 1.5 | 10.0 ± 1.0 | 17.4 ± 5.6 |
| 5932 | 12.7 ± 2.3 | 11.6 ± 1.2 | 2.9 ± 0.5 | 10.0 ± 2.4 | 12.4 ± 2.7 |
| 5937 | 17.9 ± 2.1 | 18.8 ± 1.7 | 3.5 ± 1.2 | 11.4 ± 1.6 | 24.2 ± 7.1 |
| 5945 | 20.1 ± 3.1 | 27.9 ± 2.6 | 13.3 ± 0.8 | 24.9 ± 2.0 | ND |
| 5946 | 33.6 ± 2.6 | 34.2 ± 2.5 | ND | ND | ND |
| 6037 | 14.0 ± 3.5 | 9.4 ± 0.8 | ND | ND | ND |

It has previously been demonstrated that a single point mutation within the catalytic domain of PLK1 confers resistance to ATP-based inhibitors while retaining full catalytic activity. The Retinal Pigment Epithelial (RPE) cells generated by this group were obtained and the resistant phenotype was confirmed by cell viability assay (FIG. 6). As shown, the results confirm that WT RPE cells are sensitive to BI-2536 ($IC_{50}$=21.2 nM) while mutant RPE cells are dramatically resistant to BI-2536 (>2.5 µM). Non-peptidic PBD inhibitors were found to be able to circumvent the resistance observed by ATP-based inhibitors using this RPE cell line. Cells containing wild type and mutant (C67V) PLK1 were sensitive to lead PBD-inhibitors (SCCP ID No: 5912 (FIG. 7) and SCCP ID No: 5932 (FIG. 8)) while C67V mutant cells were resistant to BI-2536—an ATP-competitive PLK1 inhibitor (FIG. 6).

Figure 9:
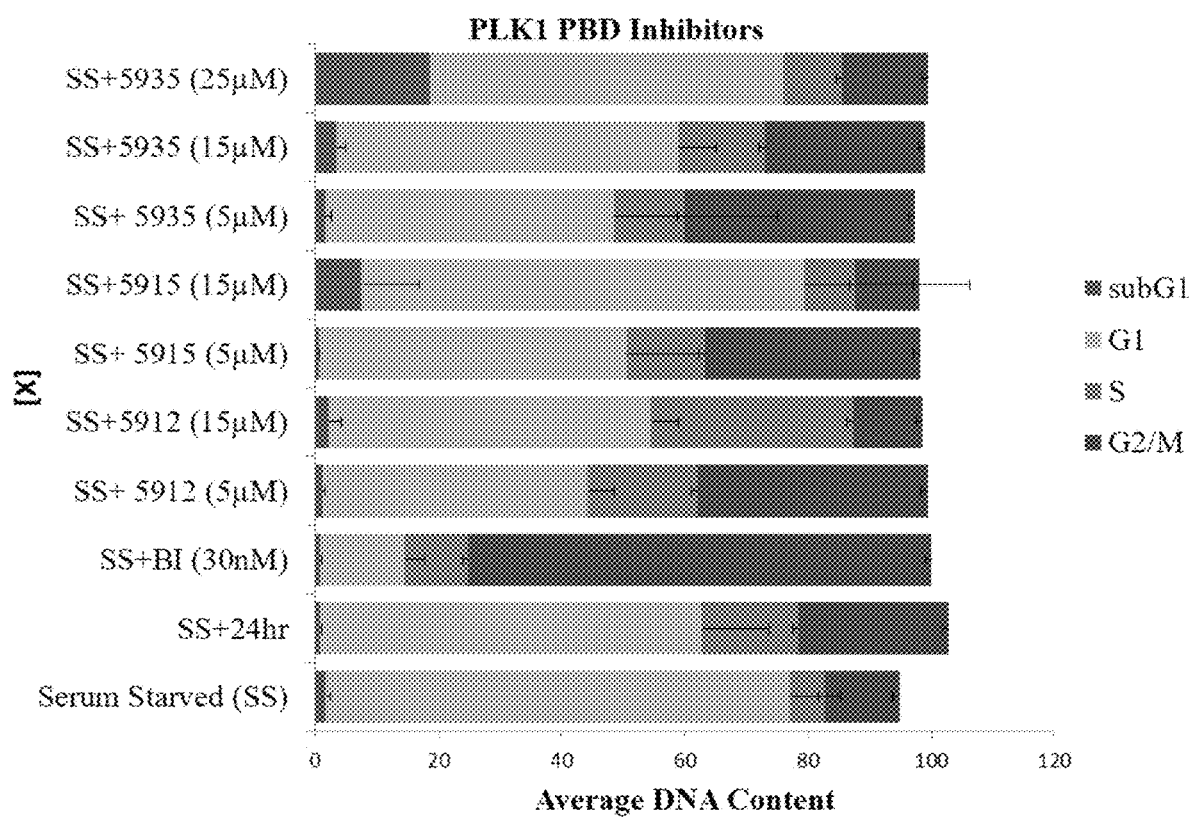
FIG. 9 provides cell cycle analysis of several disclosed PLK inhibitors in prostate cancer (PC3) cells.
Figure 10:
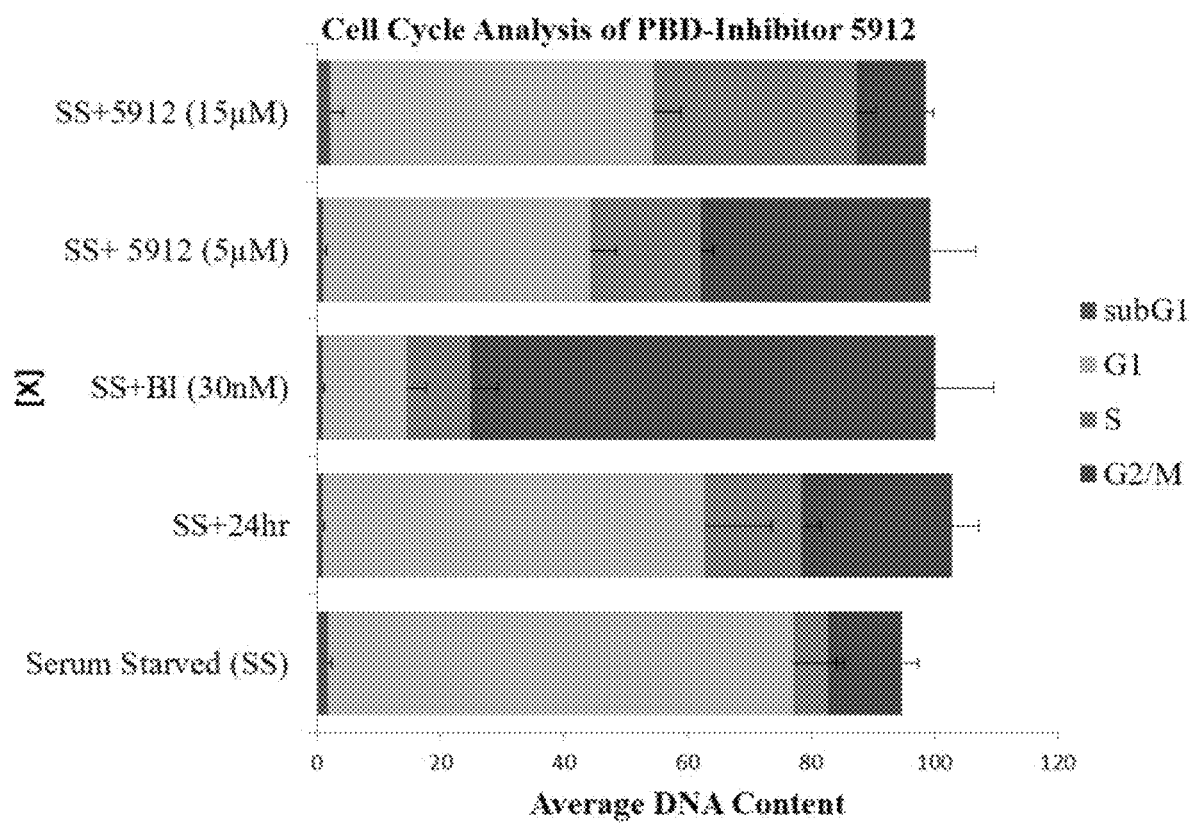
FIG. 10 provides cell cycle analysis of one small molecule PLK inhibitor (SCCP ID No. 5912) in prostate cancer (PC3) cells.

The PLK1 PBD-inhibitors were analyzed further by cell cycle analysis in PC3 cells (FIG. 9). At a concentration of 5 µM, SCCP ID No: 5912 shows moderate (13% increase relative to control) increase in G2/M population, suggesting PLK1 is being inhibited (FIG. 10). This result is modest when compared to those obtained using an ATP-competitive inhibitor (BI-2536), which shows nearly 80% of cells accumulate in G2/M. A higher concentration of SCCP ID No: 5912 (15 µM) results in a phenotype that suggests other targets are being engaged (FIG. 9). SCCP ID No: 5912 shows S phase delay (FIG. 9 and FIG. 10), implicating PLK3 inhibition at 15 µM; whereas SCCP ID Nos: 5915 and 5935 show G1 delay or arrest at 15 µM, implicating PLK2 or PLK3 inhibition. To quantify the percentage of cells actively proliferating (synthesizing their DNA) or arrested Bromodeoxyuridine (BrdU) pulse labeling was carried out and analyzed by flow cytometry. Results showed that 28.3% of cells were replicating their DNA when treated with 5 µM SCCP ID No: 5915; however, cells are arrested in G1 (BrdU+=3.6%) following treatment with 15 µM SCCP ID No: 5915.

Figure 11:
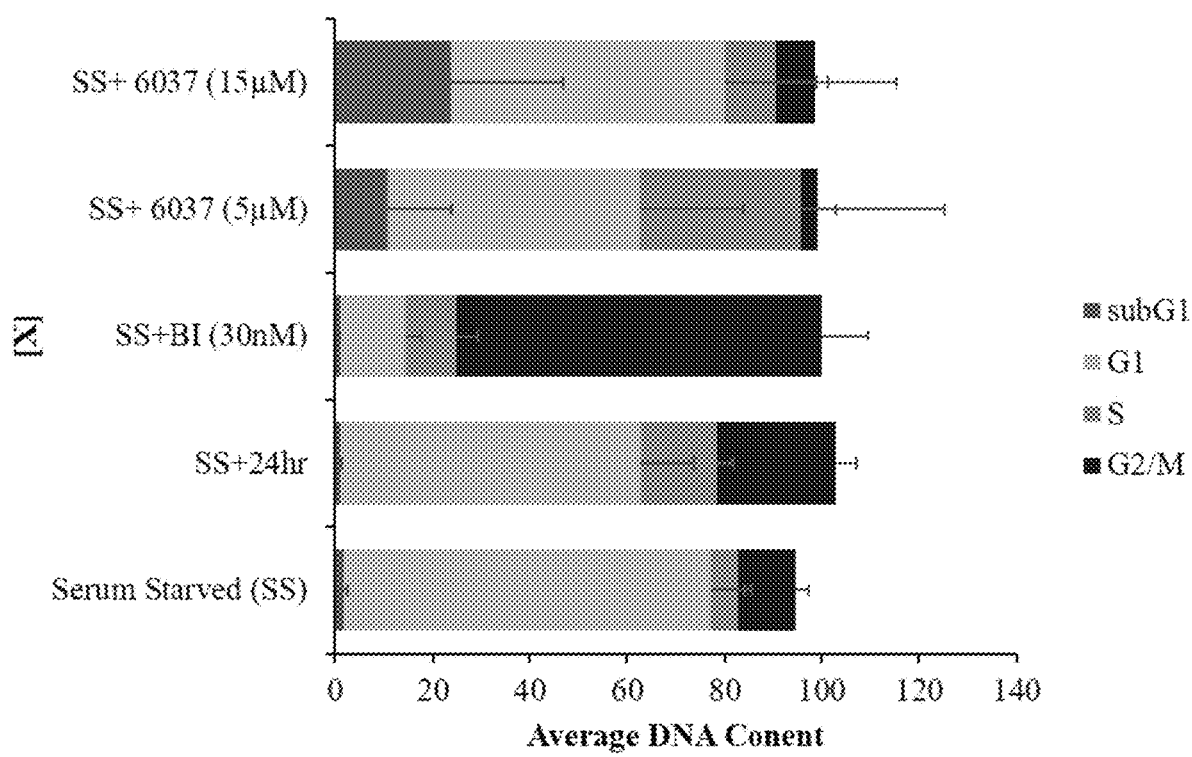
FIG. 11 provides cell cycle analysis of another small molecule PLK inhibitor (SCCP ID No. 6037) in prostate cancer (PC3) cells.

After treating PC3 cells with SCCP ID No: 6037—the least selective inhibitor (Fold Selectivity=1.6)—G1 accumulation was observed at both the lower and higher dose (FIG. 11). Upon low dose (5 µM) treatment, BrdU labeling showed that 75.7% of the cells were replicating their DNA. This suggests that the lower dose observations result from either a delay of cells exiting G1 or delayed progression through S phase, as opposed to an S-phase arrest. Like SCCP ID No: 5915, a G1 arrest was observed following the higher dose (15 µM) treatment (BrdU+=1.9%). This supports the FP data showing low PLK1 selectivity for SCCP ID No: 6037.

Figure 12:
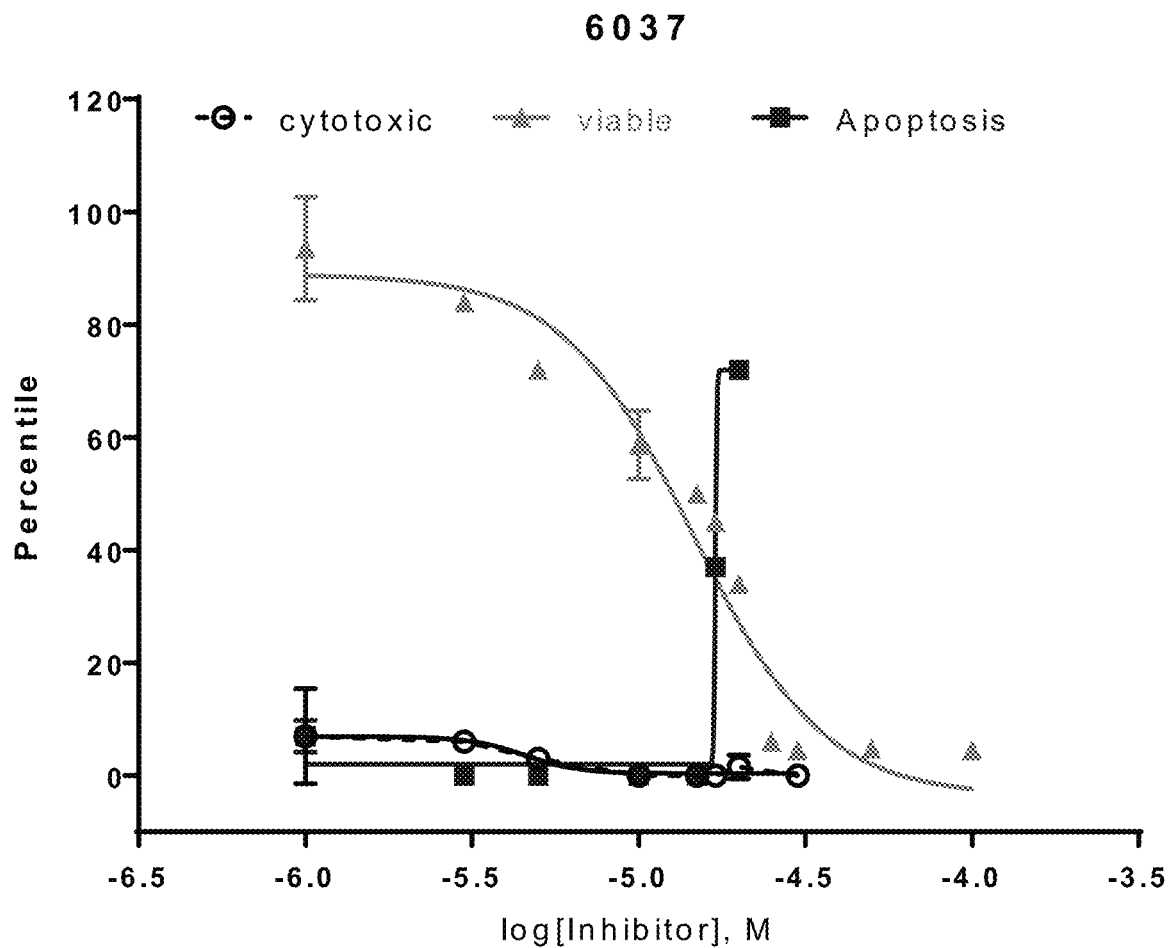
FIG. 12 provides cell viability analysis for a small molecule inhibitor (SCCP ID No. 6037) as described herein.
Figure 13:
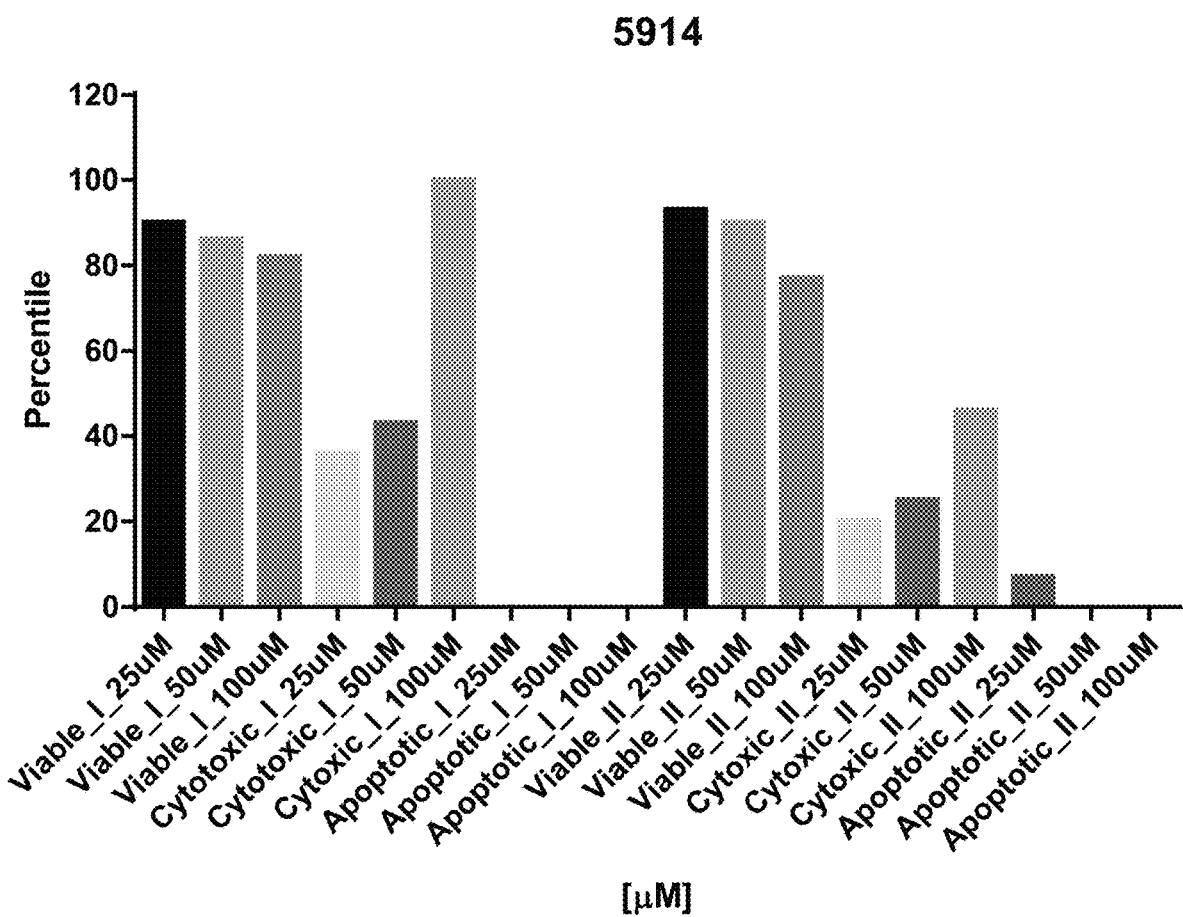
FIG. 13 provides cell viability analysis of another small molecule inhibitor (SCCP ID No. 5914) as described herein at various concentrations for both the inhibitor and the cells.
Figure 14:
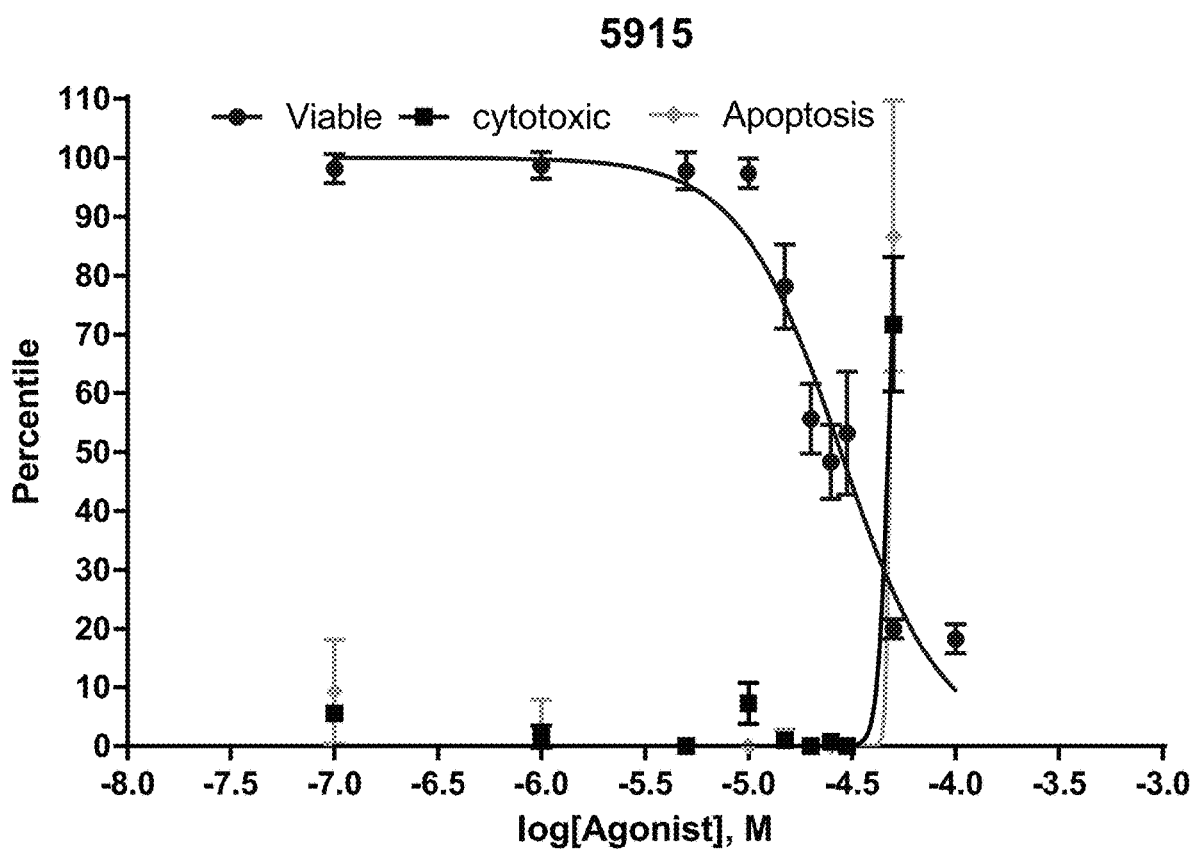
FIG. 14 provides cell viability analysis of another small molecule inhibitor (SCCP ID No. 5915) as described herein.

Additional cell viability data for the inhibitors is provided in FIG. 12-FIG. 14. For instance, FIG. 12 presents cytotoxicity, cell viability, and apoptosis data for cells treated with inhibitor SCCP ID No: 6037. The average from various assays included a cell viability of 15.6±3.4 µM, a cytotoxicity of 14.8±3.6 µM, and apoptosis of ±5.6 µM. The data of FIG. 13 relates to SCCP ID No: 5914 and the data of FIG. 14 relates to SCCP ID No: 5915.

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure, which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A method for inhibiting Polo-like Kinase proteins, the method comprising:

providing a small molecule PLK inhibitor to a medium containing one or more Polo-like Kinase proteins, wherein the small molecule PLK inhibitor has the following structure:

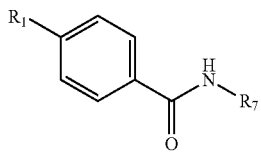

wherein $R_1$ comprises an alkyl, —O-alkyl, —S-alkyl, or —NH-alkyl, and optionally includes a terminal aryl;

$R_7$ is selected from:

b)

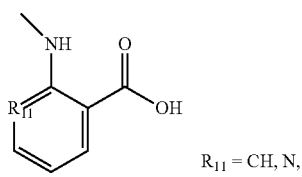

$R_{11}$ = CH, N, c)

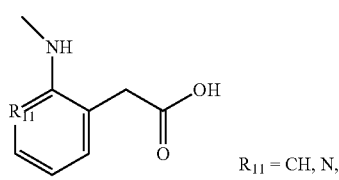

$R_{11}$ = CH, N,

-continued d)

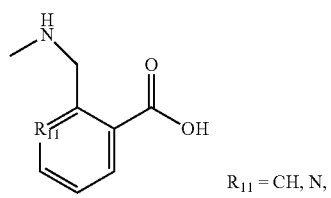

$R_{11}$ = CH, N, e)

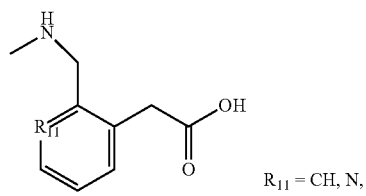

$R_{11}$ = CH, N, f)

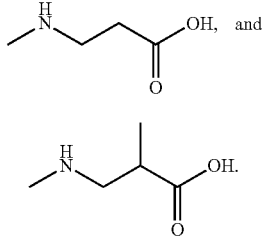

and g)

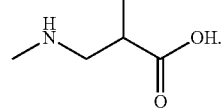

2. The method of claim 1, wherein the medium comprises a solution.

3. The method of claim 1, wherein the medium comprises one or more cells.

4. The method of claim 1, wherein the medium comprises one or more cells and the inhibitor induces apoptosis in a least a portion of the one or more cells.

5. The method of claim 1, wherein the one or more Polo-like Kinase proteins comprise PLK1.

6. The method of claim 1, wherein the one or more Polo-like Kinase proteins comprise PLK3.

7. The method of claim 3, wherein the one or more cells comprise HeLa cervical cancer cells, PTEN-deficient prostate cancer (PC3) cells, KRAS mutant lung cancer (A-549) cells, or a combination thereof.

8. The method of claim 1, wherein $R_1$ comprises a C10 to C12 alkyl.

9. The method of claim 1, wherein the small molecule PLK inhibitor has an atomic mass of about 1000 Daltons or less.

10. The method of claim 1, wherein the small molecule PLK inhibitor has an atomic mass of about 500 Daltons or less.

11. The method of claim 1, wherein the small molecule PLK inhibitor has a polar surface area of about 200 Å or less.

12. The method of claim 1, wherein the small molecule PLK inhibitor has a polar surface area of about 100 Å or less.

13. A method for inhibiting Polo-like Kinase proteins, the method comprising:

providing a small molecule PLK inhibitor to a medium containing one or more Polo-like Kinase proteins, wherein the small molecule PLK inhibitor has the structure of one or more of:

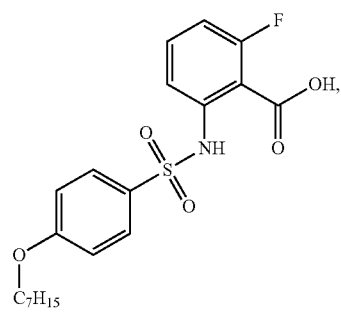

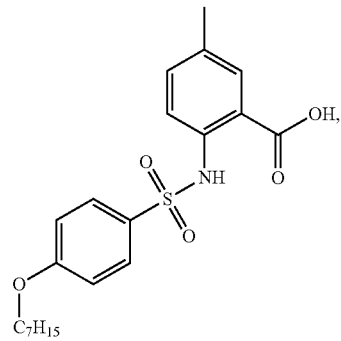

-continued

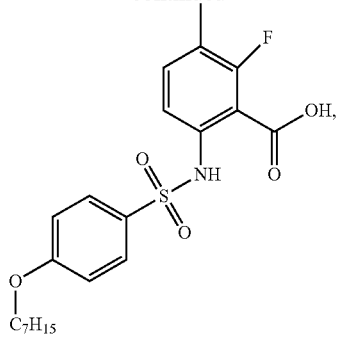

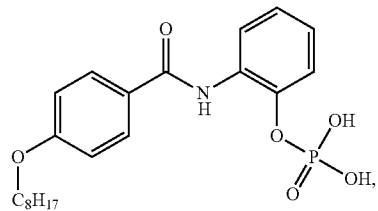

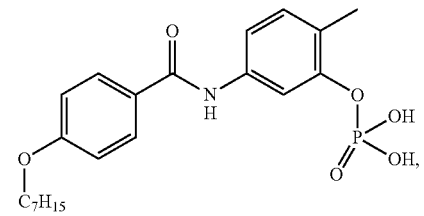

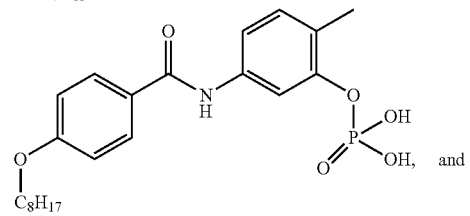 and

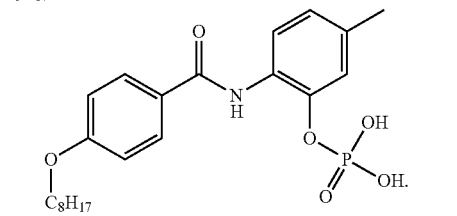

* * * * *